(12) United States Patent
Bunick

(10) Patent No.: US 7,955,652 B2
(45) Date of Patent: Jun. 7, 2011

(54) ENROBED CORE

(75) Inventor: Frank J. Bunick, Randolph, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 124 days.

(21) Appl. No.: 11/946,967

(22) Filed: Nov. 29, 2007

(65) Prior Publication Data
US 2008/0069880 A1    Mar. 20, 2008

Related U.S. Application Data

(63) Continuation of application No. 11/643,058, filed on Dec. 21, 2006, now abandoned, which is a continuation of application No. 10/146,471, filed on May 15, 2002, now Pat. No. 7,169,450.

(51) Int. Cl.
*B05D 3/00* (2006.01)

(52) U.S. Cl. ........ 427/322; 427/414; 427/299; 427/420; 427/415

(58) Field of Classification Search .................. 424/451, 424/686, 687, 474, 456; 106/162.1; 428/402.21, 428/35.7; 427/322, 414, 299, 420, 415
See application file for complete search history.

(56) References Cited

U.S. PATENT DOCUMENTS

| | | |
|---|---|---|
| 2,624,163 A | 1/1953 | Stim |
| 3,185,626 A | 5/1965 | Baker |
| 4,028,024 A | 6/1977 | Moreland |
| 4,543,370 A | 9/1985 | Porter et al. |
| 4,643,894 A | 2/1987 | Porter et al. |
| 4,655,840 A | 4/1987 | Wittwer et al. |
| 4,673,438 A | 6/1987 | Wittwer et al. |
| 4,683,256 A | 7/1987 | Porter et al. |
| 4,725,441 A | 2/1988 | Porter et al. |
| 4,790,881 A | 12/1988 | Wittwer et al. |
| 4,802,924 A | 2/1989 | Woznicki et al. |

(Continued)

FOREIGN PATENT DOCUMENTS

CA    1049466 A    2/1979

(Continued)

OTHER PUBLICATIONS

Ansel, Howard, C., et al.: Pharmaceutical Dosage Forms and Drug Delivery Systems. Lippincott Williams & Wilkins, 1999, p. 182.

(Continued)

*Primary Examiner* — Rena L Dye
*Assistant Examiner* — Ellen S Wood
(74) *Attorney, Agent, or Firm* — William E. McGowan

(57) ABSTRACT

An enrobed a core, such as a tablet core, that has a coating made of one or more patterned films each having portions that are visually distinct (e.g., differently colored) from one another and having a transition line segment between these visually distinct portions. At least a portion of an outer surface of the core is covered with the film or films, such that the transition line segments form a substantially continuous transition line on the coating and a film seam is formed which is different from the transition line. Where the patterned films are bi-colored, the resulting enrobed core can be bi-colored, or the resulting enrobed core can have a coating with at least four visually distinct portions alternately arranged thereon, thereby forming a "checkerboard" pattern on the coating. In either case, the film seam of the coating is different from the transition line of the coating.

19 Claims, 20 Drawing Sheets

U.S. PATENT DOCUMENTS

| | | |
|---|---|---|
| 4,820,524 A | 4/1989 | Berta |
| 4,828,841 A | 5/1989 | Porter et al. |
| 4,851,226 A | 7/1989 | Julian et al. |
| 4,906,478 A | 3/1990 | Valentine et al. |
| 4,973,480 A | 11/1990 | Hermelin et al. |
| 5,075,114 A | 12/1991 | Roche |
| 5,089,270 A | 2/1992 | Hampton et al. |
| 5,146,730 A | 9/1992 | Sadek et al. |
| 5,200,191 A | 4/1993 | Steele et al. |
| 5,213,738 A | 5/1993 | Hampton et al. |
| 5,275,822 A | 1/1994 | Valentine et al. |
| 5,296,233 A | 3/1994 | Batista et al. |
| 5,317,849 A | 6/1994 | Sauter |
| 5,415,868 A | 5/1995 | Smith et al. |
| 5,427,614 A | 6/1995 | Wittwer et al. |
| 5,459,983 A | 10/1995 | Sadek et al. |
| 5,460,824 A | 10/1995 | LeBrun et al. |
| 5,464,631 A | 11/1995 | Hoover et al. |
| 5,489,436 A | 2/1996 | Hoy et al. |
| 5,511,361 A | 4/1996 | Sauter |
| 5,609,010 A | 3/1997 | Sauter |
| 5,624,681 A | 4/1997 | Tanner et al. |
| 5,630,871 A | 5/1997 | Jordan |
| 5,672,300 A | 9/1997 | Schurig et al. |
| 5,795,588 A | 8/1998 | Sauter |
| 5,824,338 A | 10/1998 | Jacobs et al. |
| 6,080,426 A | 6/2000 | Amey et al. |
| 6,103,260 A | 8/2000 | Luber et al. |
| 6,113,945 A | 9/2000 | Jacobs et al. |
| 6,117,479 A | 9/2000 | Hogan et al. |
| 6,126,767 A | 10/2000 | Smith et al. |
| 6,274,162 B1 | 8/2001 | Steffenino et al. |
| 6,352,719 B1 | 3/2002 | Brown et al. |
| 6,482,516 B1 * | 11/2002 | Sadek et al. ............ 428/402.24 |
| 2003/0224090 A1 | 12/2003 | Pearce et al. |

FOREIGN PATENT DOCUMENTS

| | | |
|---|---|---|
| EP | 0 319 318 A2 | 6/1989 |
| JP | 63-145775 | 6/1988 |
| JP | 5-500514 | 4/1991 |
| JP | 4-211608 | 9/1991 |
| JP | 3205340 | 2/1994 |
| JP | 2000-508552 | 10/1997 |
| JP | 11-090316 A | 4/1999 |
| JP | 2002-293734 | 3/2005 |
| WO | WO 97/37629 A1 | 10/1997 |
| WO | WO 03/26612 A2 | 4/2003 |
| WO | WO 03/26628 A2 | 4/2003 |

OTHER PUBLICATIONS

Remington's Practice of Pharmacy, Martin & Cook, 17$^{th}$ ed., pp. 1625-1630.

USP24, 200 Version, 19-20 and 856 (1999).

* cited by examiner

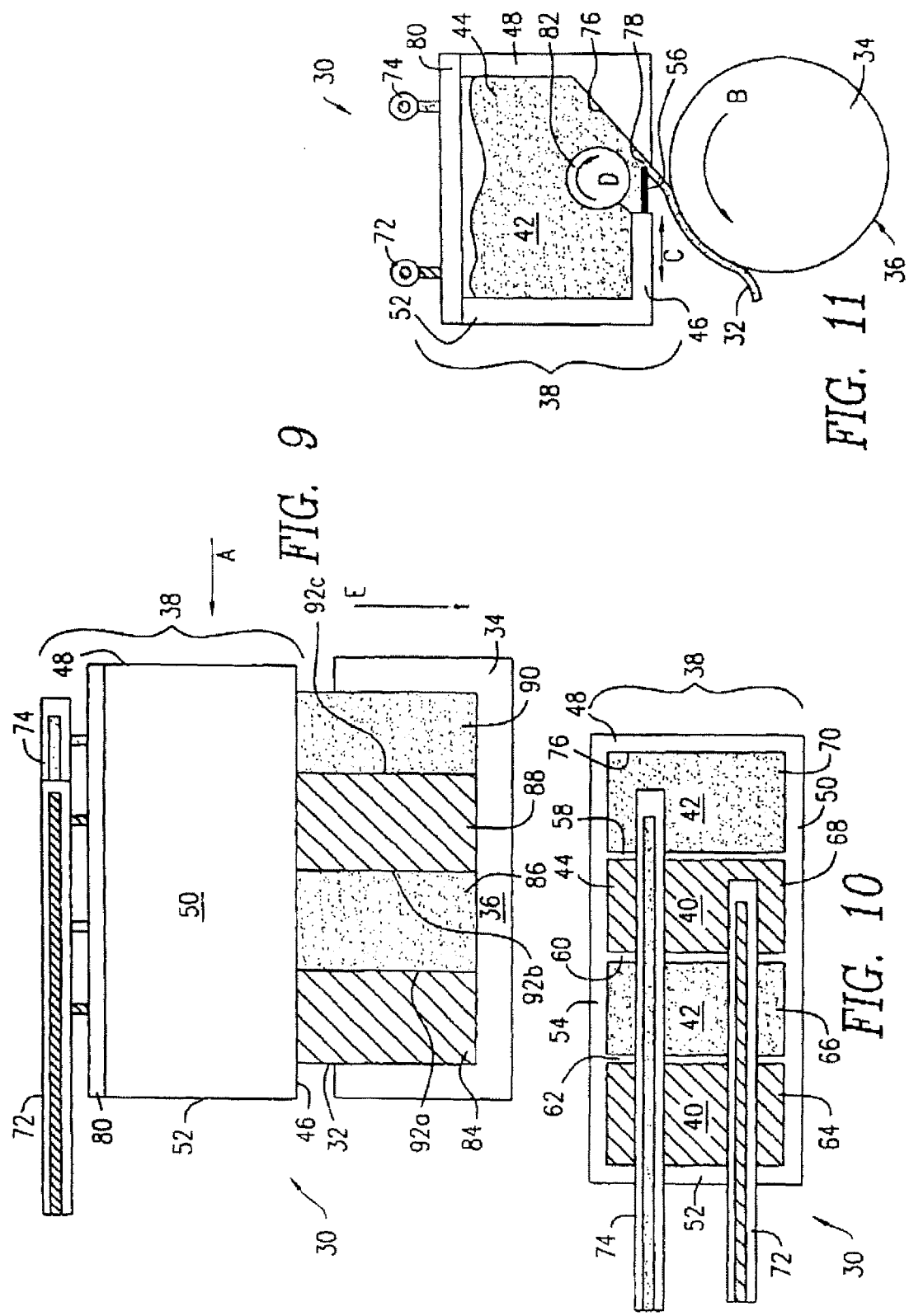

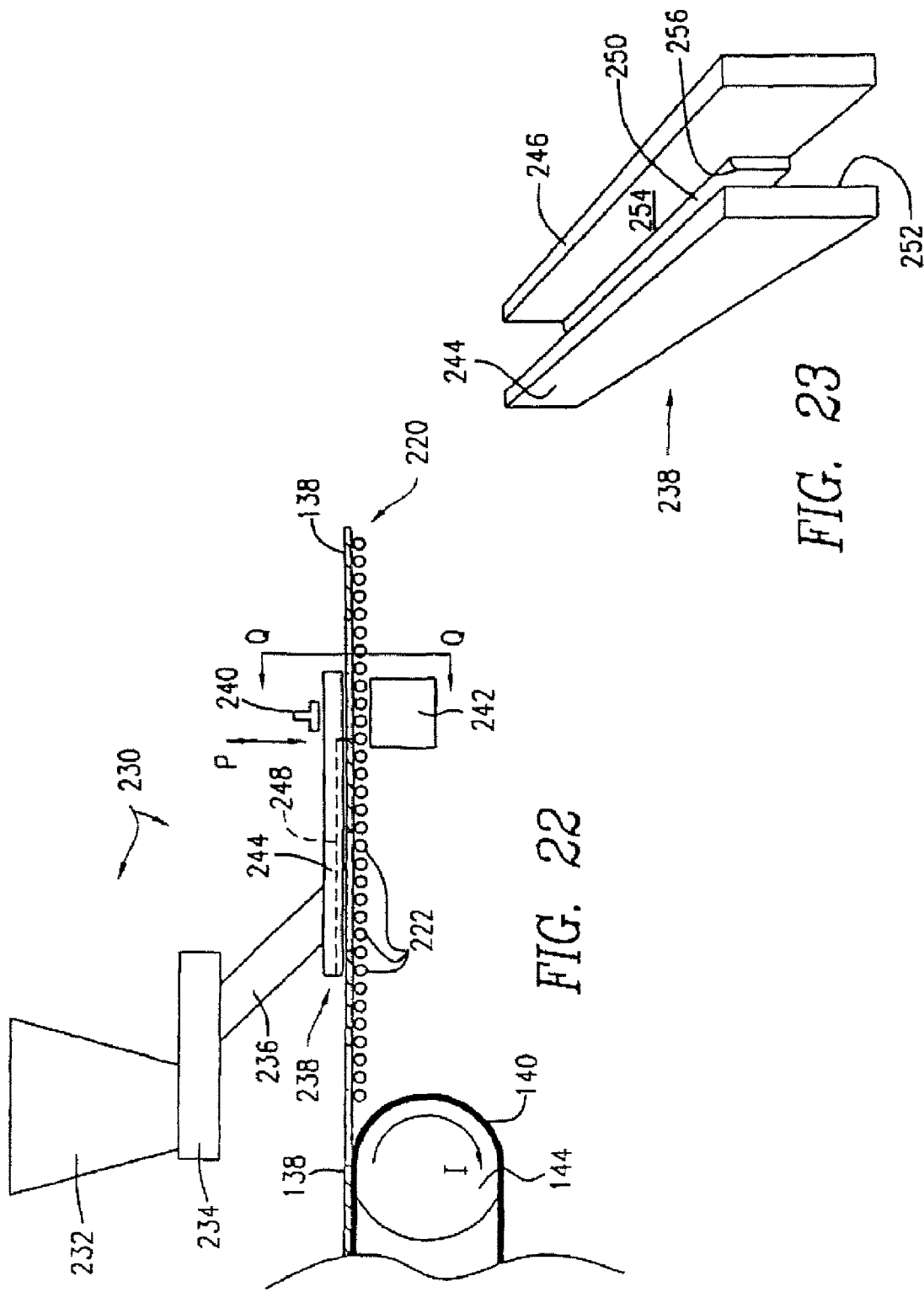

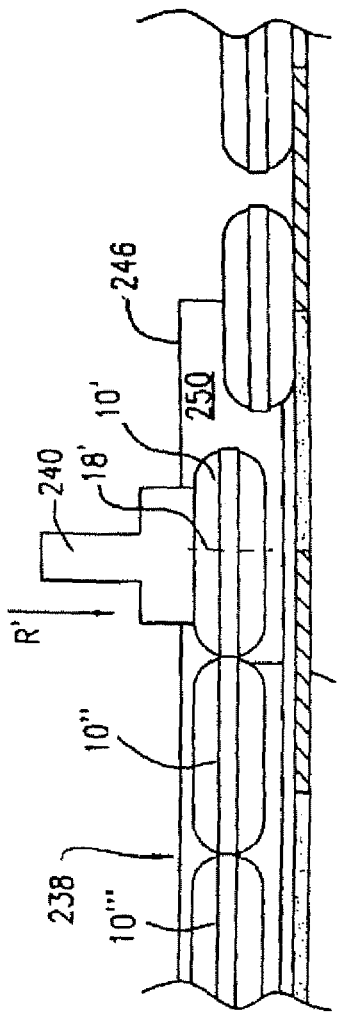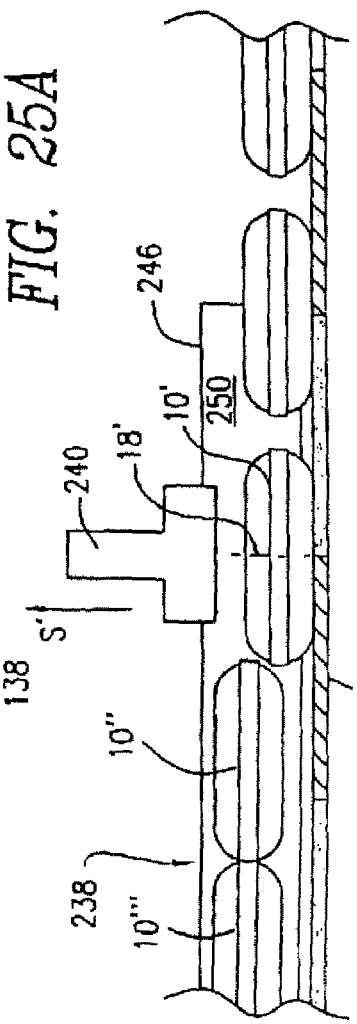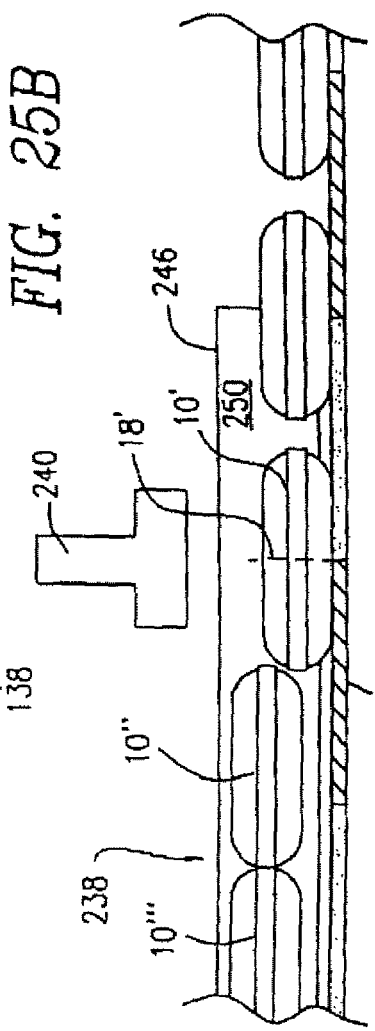
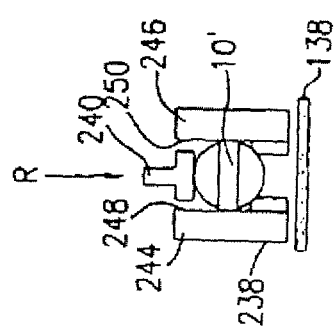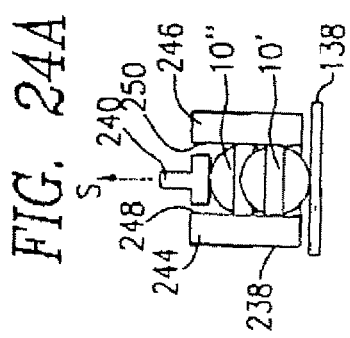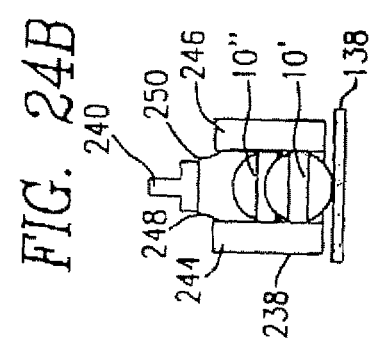

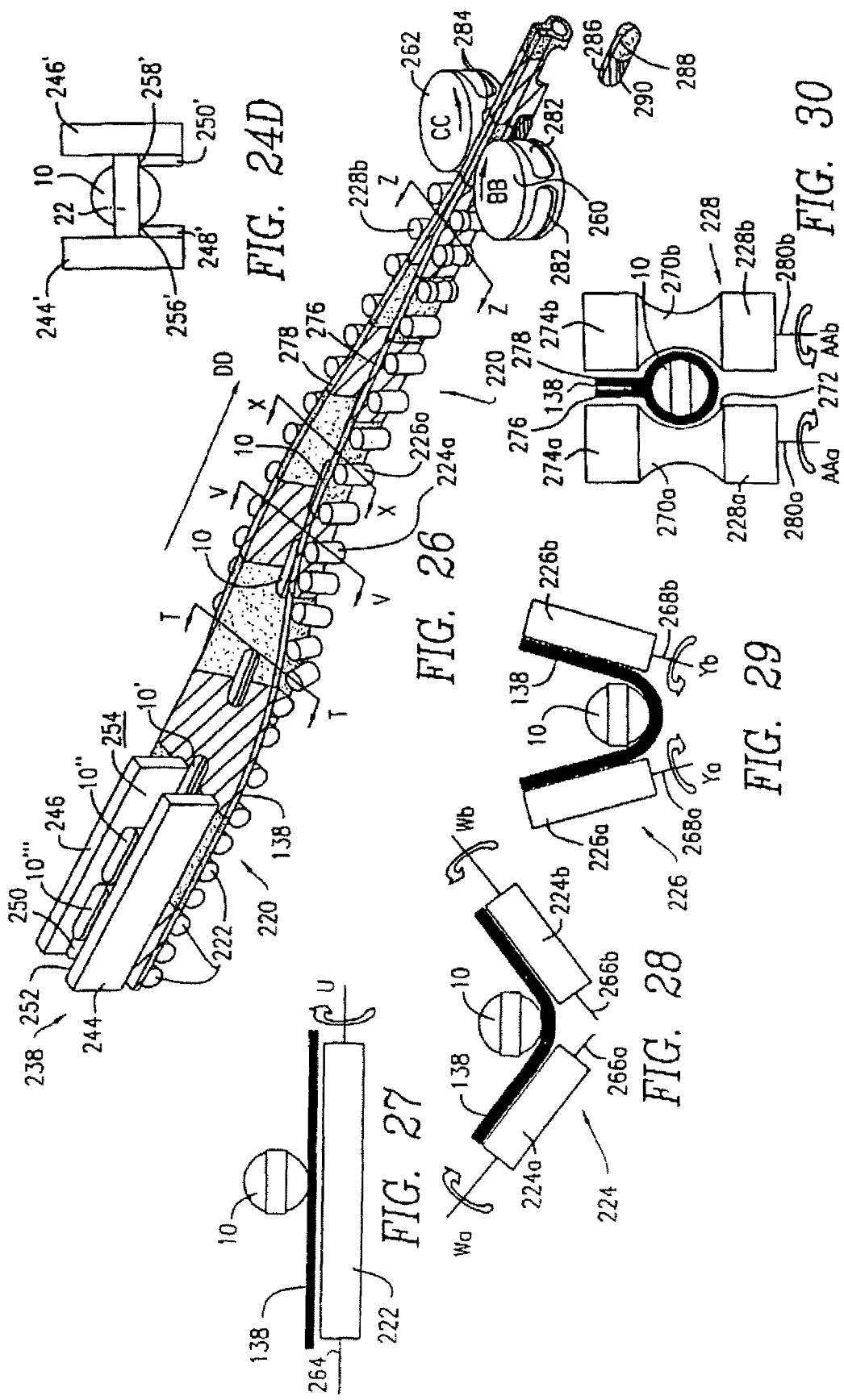

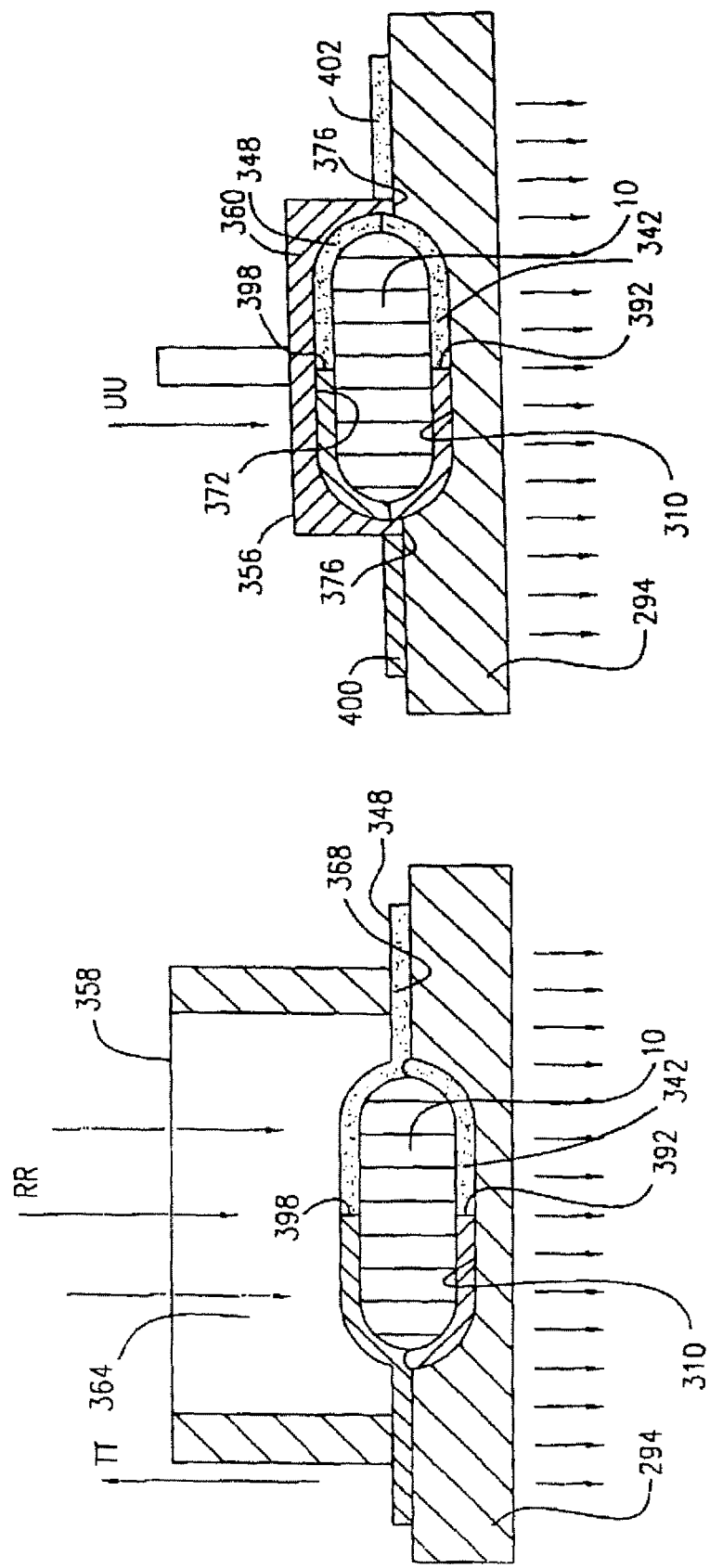

ENROBED CORE

CROSS-REFERENCE TO RELATED APPLICATION

This application is a continuation of U.S. application Ser. No. 11/643,058, filed Dec. 21, 2006 now abandoned, which application is a continuation of U.S. application Ser. No. 10/146,471 filed 15 May 2002 now U.S. Pat. No. 7,169,450, which is incorporated by reference in its entirety, and claims the benefit thereof. This application is also related to U.S. Pat. No. 6,946,156, which issued on 20 Sep. 2005.

FIELD OF THE INVENTION

The present invention relates to an enrobed core, such as a tablet core, having a patterned coating formed by one or more patterned films.

BACKGROUND OF THE INVENTION

Various oral dosage forms have been developed over the years for pharmaceuticals and dietary supplements. Among the more popular oral dosage forms are tablets, capsules and, most recently, gelcaps. Tablets are compressed or molded solid dosage forms of any size or shape. Solid, generally oblong-shaped tablets may sometimes be referred to as caplets. Tablets remain popular with consumers, however uncoated tablets suffer from drawbacks such as medicinal taste, a tendency to powder or flake (i.e., physical disintegration) when packaged in bottles, and/or the perception by consumers that they are not easy to swallow. These limitations are eliminated by coating the tablets with a polymeric coating.

During most of the 20th century, hard gelatin capsules were a popular dosage form for prescription and over-the-counter (OTC) drugs. Capsules are hard shell compartments made of two halves, including a body and a cap, wherein the cap partially and snugly overlaps with the body to enclose a dosable drug ingredient therein. The enclosed dosable ingredient is most often is a powder, liquid, paste or similar non-solid form.

Generally, empty hard shell capsules are produced by a conventional dip-molding process such as that which is described on page 182 of "Pharmaceutical Dosage Forms and Drug Delivery Systems, $7^{th}$ Ed.", (1999) by Howard C. Ansel, Loyd V. Allen Jr., and Nicholas G. Popovich, published by Lippincott Williams & Wilkins, Baltimore, Md. Consumers have found that such capsules are aesthetically pleasing, easy to swallow and mask the medicine taste of the drug contained therein. In addition, the bodies and caps of such capsules are often produced in different colors, resulting in a bi-colored capsule product having enhanced aesthetic appeal, as well as improved product identification and brand recognition by consumers. Many patients preferred capsules over coated or uncoated tablets, prompting pharmaceutical manufacturers to market certain products in capsule form even when they were also available in tablet form. However, due to potential tampering concerns, capsules are no longer a preferred delivery choice for consumer (i.e., over-the-counter) pharmaceuticals.

One alternative to capsule products are caplets, which are solid, oblong tablets that are often coated with various polymers such as cellulose ethers to improve their aesthetics, stability, and swallowability. Typically, such polymers are applied to the tablets either from solution in organic solvents, or from aqueous dispersion via spraying. Still other methods involve spray coating tablets with a gelatin coating solution. See, e.g., U.S. Pat. Nos. 4,973,480 and 6,113,945. However, such spray-coated tablets lack the glossy surface and elegance of the hard gelatin capsules. Additionally, it is not commercially feasible to spray-coat a tablet with a different color coating on each end.

Another alternative to capsule products are "gelcaps," which are elegant, consumer-preferred dosage forms comprising solid tablets covered with a glossy gelatinous coating. Currently, gelcaps are among the most popular oral dosage forms. Several methods of producing gelcaps have been developed in an effort to provide tamper-proof capsule-like products. One category of such methods involve dipping tablets, one half at a time, into gelatin coating solutions, which can be of two different colors, see, e.g., U.S. Pat. No. 4,820,524, or dipping tablets of a first color halfway into a into gelatin coating solution of a second color, see, e.g., U.S. Pat. No. 6,113,945. Another category of such methods involves shrink-fitting the capsule halves onto a tablet form. See, for example, U.S. Pat. Nos. 5,415,868, 6,126,767, 5,464,631, 5,460,824, 5,317,849, 5,511,361, 5,609,010, 5,795,588 and 6,080,426, and International Patent Appln. Publication No. WO 97/37629. Another method involves sealing the body and cap of the capsule at the overlapping seam therebetween. See U.S. Pat. No. 5,824,338. Another method of producing gelcaps is via an enrobing process wherein two separate films made of gelatinous material are applied to opposite sides of a tablet by a pair of rotary dies. A detailed description of this process is provided, for example, in U.S. Pat. Nos. 5,146,730 and 5,459,983, and the entire contents and disclosures of both of these patents are hereby incorporated herein by reference.

Briefly, in the aforesaid rotary die process, two circular dies each having a circumferential surface are positioned such that the surfaces are in abutting relationship with one another, thereby forming a nip therebetween. Each of the dies have a series of matching recesses on their circumferential surfaces. As the dies rotate, the films are joined and fused together, at the nip between the dies where a pair of matching recesses form a pocket into which a tablet is dropped by a metered feed mechanism. As the dies continue to rotate, the tablet urges the films into the interior of the recesses in the dies, and the tablet is thereby securely enveloped and enrobed by the films, while the films continue to be joined and fused together about the tablet by the dies. Simultaneously with the fusing of the films about the tablet, the enrobed tablet is pinch-cut from the films by the rotary dies, whereupon it separates from the films in the form of an individual enrobed tablet. If the films used are of two different colors, the resulting enrobed tablets are bi-colored having a color transition line that is commensurate with the seam between the films. Thus, while foregoing process produces tamper-proof bi-colored enrobed tablets, the color transition of such products will always be commensurate with the seam between the films.

Each of the foregoing methods for producing tamper-proof coated tablets suffer from several shortcomings, including uneven color of the capsule halves and/or coatings, uneven thickness of the capsule halves and/or coatings, and the creation of raised seams between capsule halves and/or coatings. In addition, the bi-colored products resulting from the aforesaid methods have a line defined by the color transition, which is always the same as the line defined by the seam between the capsule halves and/or coatings.

U.S. Pat. No. 5,672,300 discloses the production and use of striped and patterned films with the foregoing rotary die process to produce patterned enrobed tablets. The striped films disclosed therein are produced by depositing stock film forming material of a first color from a first spreader box to form a base film and then, using a second spreader box, adding stripes of a differently colored stock material onto the base film. Films having different patterns, including stripes and/or marbleized, are created by oscillating the second spreader box relative to the first spreader box. The gelcaps produced by this process have multiple stripes, or a marbleized pattern, rather than simply being bi-colored (i.e., one half being one color and the other half being a second color). Films prepared by this process suffer from the limitation of having multiple layers, with increased total film thickness in the area where the second film material is applied. The increased film thickness creates an uneven appearance and feel to the surface, and retards dissolution, which is undesirable for immediate release dosage forms. Thus, there is still a need to produce bi-colored enrobed tablets that are enrobed with films according to the rotary die process and that have color transitions that are not commensurate with the seam between the films.

SUMMARY OF THE INVENTION

The present invention relates to an enrobed core, such as a tablet core, that has a coating made of a patterned film having portions that are visually distinct (e.g., differently colored) from one another and having a transition line segment between such visually distinct portions. More particularly, the film at least partially covers an outer surface of the core, such that the transition line segment forms a substantially continuous transition line on the coating and such that a film seam is formed which is different from the transition line. That is, the film seam lies substantially in a first reference plane that passes through the core, while the transition line segment lies substantially in a second reference plane that passes through the core and intersects the first reference plane.

Alternatively, the coating is formed from two films, each of which has portions that are visually distinct from one another and a transition line segment between such visually distinct portions. The outer surface of the core is covered with the two films such that the two transition line segments cooperate to form a substantially continuous transition line on the coating and a film seam is formed on the coating which is different from the transition line. That is, the film seam lies substantially in the first reference plane that passes through the core, while the transition line segment lies substantially in the second reference plane that passes through the core and intersects the first reference plane.

In addition, where the patterned films are bi-colored, the resulting enrobed core can be bi-colored with the film seam of the coating lying substantially in the first reference plane and the transition line between the two colors thereof lying substantially in the second reference plane. The resulting enrobed core may, instead, have four alternately arranged colored portions, two of which are of a first color and the other two of which are of a second color, thereby resulting in a "checkerboard" effect.

Where the portions of each of the two patterned films are all visually distinct from one another, the resulting enrobed core can have a coating with at least four portions each having a different visual distinction (e.g., color). The film seam of the coating would still lie substantially in the first reference plane and the transition line would be different from the film seam and would still lie substantially in the second reference plane.

BRIEF DESCRIPTION OF THE DRAWINGS

For a better understanding of the present invention, reference is made to the following detailed description of several exemplary embodiments considered in conjunction with the accompanying drawings, in which:

FIG. 9 is a simplified, schematic elevational front view of film casting apparatus in accordance with a first embodiment of the present invention;

FIG. 10 is a simplified, schematic top plan view of the film casting apparatus of FIG. 9, showing the interior chambers of the slit extruder;

FIG. 11 is a simplified, schematic elevational left side view of the film casting apparatus of FIG. 9, looking in the direction of arrow A;

FIG. 22 is a simplified, schematic elevational side view of a core dispensing means that is part of an alternative core enrobing apparatus in accordance with a third embodiment of the present invention;

FIG. 23 is a schematic perspective view of the core positioning slat shown in FIG. 22;

FIGS. 24A-24D are simplified, schematic elevational front views of the core positioning slat, core plunger, film and cores, as viewed from the position of line Q-Q in FIG. 22 and looking in the direction of the arrows, showing the operation of the core plunger to position cores onto the film;

FIG. 25A is a simplified, schematic elevational side view of the core positioning slat, core plunger, film, and cores, shown in FIG. 24A;

FIG. 25B is a simplified, schematic elevational side view of the core positioning slat, core plunger, film, and cores, shown in FIG. 24B;

FIG. 25C is a simplified, schematic elevational side view of the core positioning slat, core plunger, film, and cores, shown in FIG. 24C;

FIG. 26 is a simplified, schematic perspective view of the conveyor system and the rotary die of the third embodiment of the present invention, as well as the enrobed core products produced thereby;

FIG. 27 is a simplified, schematic elevational view of a single roller of the conveyor system, the film and a core positioned thereon, as seen from the position of line T-T in FIG. 26 and looking on the direction of the arrows, showing the horizontal orientation of the roller;

FIG. 28 is a simplified, schematic elevational view of a first pair of rollers of the conveyor system, the film and a core positioned thereon, as seen from the position of line V-V in FIG. 26 and looking on the direction of the arrows, showing the slightly angled orientation of the rollers;

FIG. 29 is a simplified, schematic elevational view of a second pair of rollers of the conveyor system, the film and a core positioned thereon, as seen from the position of line X-X in FIG. 26 and looking on the direction of the arrows, showing the substantially angled orientation of the rollers;

FIG. 30 is a simplified, schematic elevational view of a third pair of rollers of the conveyor system, the film and a core positioned thereon, as seen from the position of line Z-Z in FIG. 26 and looking on the direction of the arrows, showing the different configuration of these rollers and their vertical orientation;

FIG. 42 is a partial, schematic, cross-sectional elevational side view of a sixth station of the apparatus of the fourth embodiment, with the near cross-sectional half cut away therefrom, showing how the second film is cooled and molded about the core;

FIG. 43 is a partial, schematic, cross-sectional elevational side view of a seventh station of the apparatus of the fourth embodiment, with the near cross-sectional half cut away therefrom, showing how the second film is cut away from the perimeter of the fully enrobed core.

DETAILED DESCRIPTION OF THE INVENTION

Figure 1A:
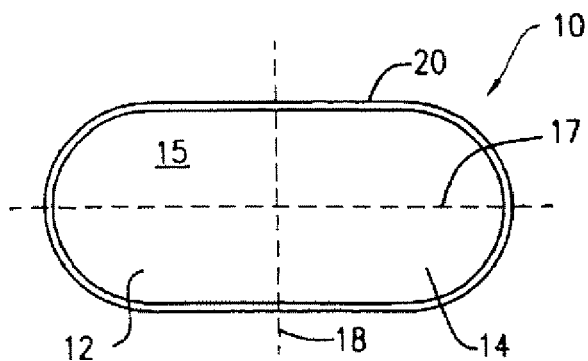
FIG. 1A is an enlarged, schematic top plan view of an oblong convex core of a first configuration, the bottom plan view being identical thereto.
Figure 1B:
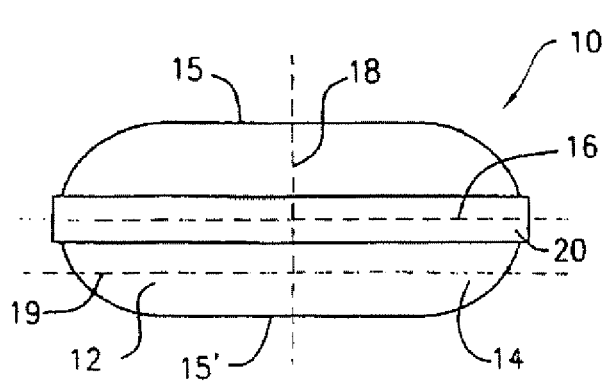
FIG. 1B is an enlarged, schematic elevational side view of the oblong convex core of FIG. 1A, the opposite elevational side view being identical thereto.
Figure 2:
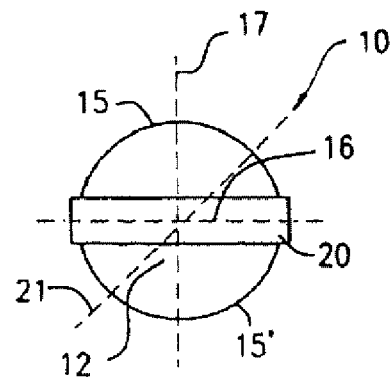
FIG. 2 is an enlarged, schematic elevational end view of the oblong convex core of FIGS. 1A and 1B, the opposite elevational end view being identical thereto.

As used hereinafter, "core" shall mean a solid dosage form of any size or shape. Suitable cores include compressed or molded tablets, hard and soft capsules, confectionery based forms such as for example lozenges, nougats, or fondants, and the like. Cores are available in various shapes and configurations. For example, FIGS. 1A, 1B and 2 show an oblong convex core 10 which has an oblong shape and two rounded ends 12, 14, as viewed from the top, bottom or sides (see FIGS. 1A and 1B). The oblong convex core 10 may also have two oppositely positioned convex surfaces 15, 15' and a raised portion therebetween, referred to as a land 20 (shown most clearly in FIGS. 1B and 2).

It is noted that the length of the oblong core 10 is an imaginary line (not shown per se, but which is commensurate with a portion of the dotted line 16 that is within the core 10 shown in FIG. 1B) which extends the distance between the ends 12, 14 of the oblong core 10. The height of the oblong core 10 is another imaginary line (not shown per se, but which is commensurate with a portion of the dotted line 18 that is within the core 10 shown in FIG. 1B) which extends the distance between the two opposite convex surfaces 15, 15' of the core 10, midway of the length. The width of the oblong core is a third imaginary line (not shown per se, but which is commensurate with a portion of the dotted line 16 that is within the core 10 shown in FIG. 2) which extends the distance between opposite sides of the core 10, perpendicular to and midway of the core's length and height (and which may intersect the land 20 of the core 10, if present).

To facilitate discussion hereinafter of the position of the films and color transitions that are applied to the enrobed core products, certain reference planes will now be defined in relation to the core 10 and its length, height and width. It is noted that while a number of different references planes may be defined in relation to the oblong core 10, the methods, apparatus and products of the present invention will be discussed primarily in terms of certain orthogonal planes of symmetry, as follows.

With reference to FIGS. 1B and 2, as used hereinafter, the "transverse", or "major", plane of symmetry 16 of the core 10 is the reference plane which includes the length and width of the core 10 and which is perpendicular to and substantially bisects the height of the core 10. The land 20 of the core 10, if present, may be aligned with the transverse plane of symmetry 16 (see FIGS. 1B and 2) such that the land 20 is substantially bisected along its entire length. As shown in FIG. 1B, it is noted that a portion of the core 10 which lies on one side of the transverse plane of symmetry 16 is substantially a mirror image of the remaining portion of the core 10 which lies on the opposite side of the transverse plane of symmetry 16.

With reference to FIGS. 1A and 1B, as used hereinafter, the "conjugate", or "minor" plane of symmetry 18 of the oblong core 10 is the reference plane which includes the width and height of the core 10 and which is perpendicular to and substantially bisects the length of the core 10. As with the transverse plane of symmetry 16, a portion of the core 10 which lies on one side of the conjugate plane of symmetry 18 is substantially a mirror image of the other side of the core 10 which lies on the opposite side of the conjugate plane of symmetry 18.

With reference now to FIGS. 1A and 2, a third plane of symmetry 17 includes the length and height of the core 10 and is perpendicular to and substantially bisects the width of the core 10. As with the transverse and conjugate planes of symmetry 16, 18, respectively, a portion of the core 10 which lies on one side of the third plane of symmetry 17 is substantially a mirror image of the other side of the core 10 which lies on the opposite side of the third plane of symmetry 17.

It is noted that additional reference planes can be defined, including many which are not planes of symmetry. For example, a reference plane 19 (see FIG. 1B) may be defined that is parallel to the length and width of the core 10, but does not include the length or width and does not divide the core into mirror image portions. In addition, another reference plane 21 (see FIG. 2) could be defined such that it is parallel to the length of the core 10, perpendicular to both the width and height of the core 10, but does not include any of the length, width or height of the core and does not divide the core into mirror image portions. It will be understood by a person having ordinary skill in the art that many additional possibilities exist for defining reference planes in relation to the core 10. However, the remaining description of the method, apparatus and products of the present invention will be discussed using, primarily, the transverse and conjugate planes of symmetry 16, 18, respectively.

Figure 3:
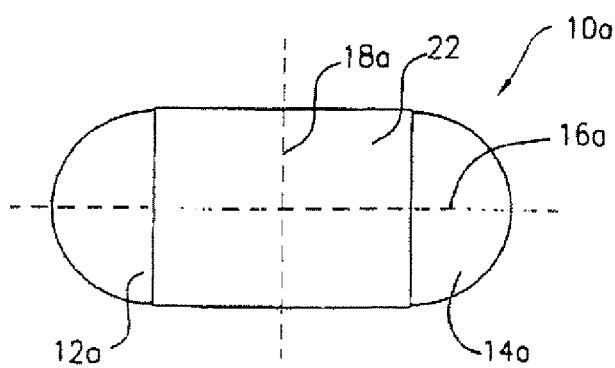
FIG. 3 is an enlarged, schematic elevational side view of an oblong convex core of a second configuration, the opposite elevational side view, as well as the top and bottom plan views, being identical thereto.
Figure 4:
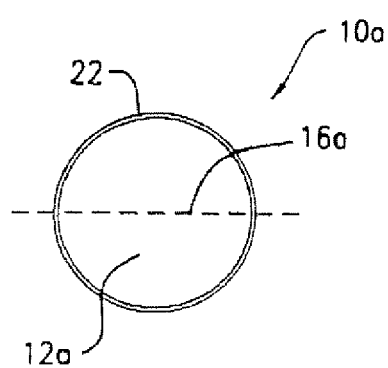
FIG. 4 is an enlarged, schematic elevational end view of the oblong convex core of FIG. 3, the opposite elevational end view being identical thereto.

With reference now to FIGS. 3-8A, examples are provided of cores having shapes and configurations different from the oblong convex core 10 shown in FIGS. 1A, 1B and 2. More particularly, as shown in FIGS. 3 and 4, an oblong convex core 10a may, alternatively, have a central cylindrical subsection 22 between the two rounded ends 12a, 14a (i.e., instead of a land 20). The core 10a shown in FIGS. 3 and 4 includes a transverse plane of symmetry 16a and a conjugate plane of symmetry 18a, the orientation of which are defined in the same manner as provided above in connection with the oblong core 10 of FIGS. 1A, 1B and 2. As can be seen from FIGS. 3 and 4, the rounded ends 12', 14' of the caplet 10' are of slightly smaller diameter than the cylindrical subsection 20.

Figure 5:
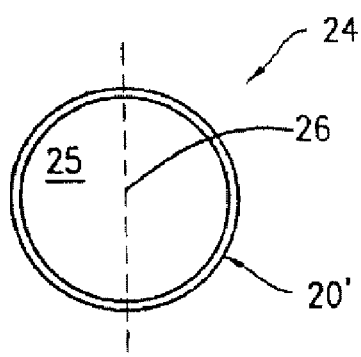
FIG. 5 is an enlarged, schematic top plan view of a round convex core, the bottom plan view being identical thereto.
Figure 6:
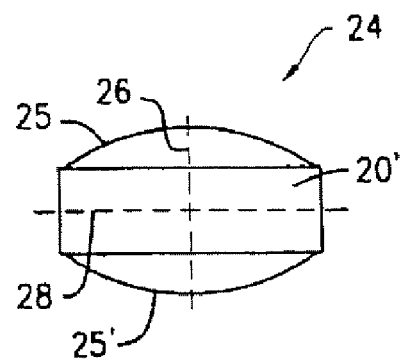
FIG. 6 is an enlarged, schematic elevational front view of the round convex core of FIG. 5, the elevational back view, as well as both elevational side views, being identical thereto.
Figure 7A:
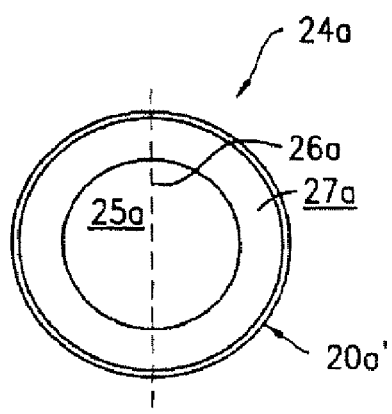
FIG. 7A is an enlarged, schematic top plan view of a round flat core with beveled edges, the schematic bottom plan view being identical thereto.

FIGS. 5, 6, 7A and 7B provide examples of "round" cores, which are cores having a generally round or circular configuration when viewed from above (see the top views shown in FIGS. 5 and 7A). In addition, while round cores have a length, a width and a height, the length and width of each round core are dimensionally interchangeable due to the generally circular configuration of each round core.

With reference in particular to FIGS. 5 and 6, a "round convex" core 24 may have two oppositely positioned convex surfaces 25, 25' which are seen most clearly from a front, back or side elevational view, such as provided in FIG. 6. The round convex core 24 includes a transverse plane of symmetry 26 and a conjugate plane of symmetry 28, the orientation of which are defined in the same manner as provided above in connection with the oblong core 10 of FIGS. 1A, 1B and 2. As also seen most clearly in FIG. 6, the round convex core 24 may also have a raised portion, or land 20', similar to the land 20 of the oblong convex core 10 of FIGS. 1A, 1B and 2.

Figure 7B:
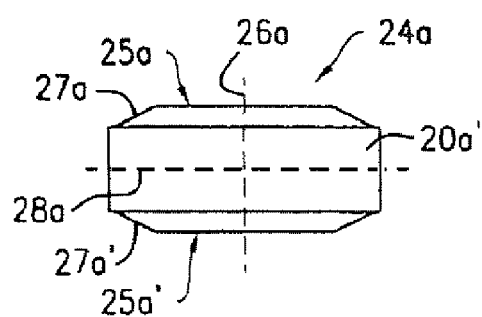
FIG. 7B is an enlarged, schematic elevational front view of the round flat core of FIG. 7A, the elevational back view, as well as both elevational side views, being identical thereto.

With reference now to FIGS. 7A and 7B, a "round flat" core 24a may have two oppositely positioned flat surfaces 25a, 25a' (i.e., rather than convex surfaces). The round flat core 24a may also have a beveled edge 27a positioned 27a proximate to one flat surface 25a (see FIGS. 7A and 7B) and another beveled edge 27a' positioned proximate to the other flat surface 25a' (see FIG. 7B) of the round flat core 24a. The round flat core 24a includes a transverse plane of symmetry 26a and a conjugate plane of symmetry 28a, the orientation of which are defined in the same manner as provided above in connection with the oblong core 10 of FIGS. 1A, 1B and 2.

Figure 8A:
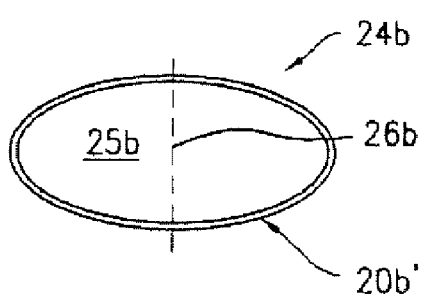
FIG. 8A is an enlarged, schematic top plan view of an oval convex core, the schematic bottom plan view being identical thereto.
Figure 8B:
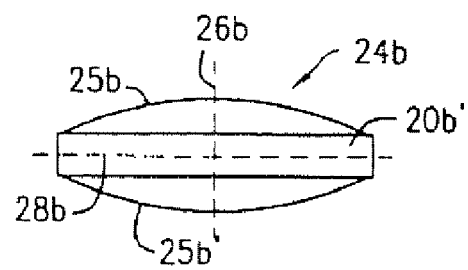
FIG. 8B is an enlarged, schematic elevational front view of the oval convex core of FIG. 8A, the elevational back view being identical thereto.

FIGS. 8A and 8B provide one example of a type of "oval" core 24b. Generally, "oval" cores are cores having have a generally oval configuration when viewed from above (see, for example, the top view shown in FIG. 8A). An "oval convex" core 24b, shown in FIGS. 8A and 8B, may have two oppositely positioned convex surfaces 25b, 25b' which are seen most clearly from a front, back or side elevational view, such as provided in FIG. 8B. The oval convex core 24b includes a transverse plane of symmetry 26b and a conjugate plane of symmetry 28b, the orientation of which are defined in the same manner as provided above in connection with the oblong core 10 of FIGS. 1A, 1B and 2. As seen most clearly in FIG. 8B, the oval convex core 24b may also have a raised portion, or land 20b', similar to the land 20 of the oblong convex core 10 of FIGS. 1A, 1B and 2.

It is noted that, while the present invention has applicability to core dosage forms of various shapes, including but not limited to the shapes shown in FIGS. 1A-8B, the remaining drawing figures and the detailed description provided hereinafter show and discuss the apparatus and methods of the present invention as applied to the oblong convex caplet 10 of the first configuration exemplified in FIGS. 1A, 1B and 2. It is understood, however, that the present invention may also be applied to differently shaped cores, including, but not limited to, the cores of other configurations, including oblong, round and oval cores, shown in FIGS. 3-8B.

The product of the present invention, which is produced by the methods and apparatus of the present invention described hereinafter, is an enrobed substrate (also referred to herein as a "core"). Such enrobed products are often referred to as "geltabs" or "gelcaps". The terms "geltabs" and "gelcaps" shall mean a substrate having at least one, non-core layer, or film, made of a film forming or gel forming substance or substances. The substrate, or core may be a compressed tablet, or other non-liquid (e.g., solid or semi-solid) dosage form.

More particularly, as will be described in further detail hereinafter, the enrobed core of the present invention is enrobed by at least one film having at least two visually distinct portions (i.e., at least two portions having different visual appearances) and at least one visual transition line between the visually distinct portions of the film. It is noted that, hereinafter, the apparatus and method of the present invention are discussed as producing enrobed cores that are substantially enrobed by the film or films and the term "substantially" shall be understood to mean that at least about 95% of the surface area of the core is covered by the film or films. Furthermore, it will be understood by those having ordinary skill in the art that the apparatus and method of the present invention may be adapted to produce enrobed core products that are at least partially covered by the film or films. The term "at least partially covered" shall be understood to mean that at least about 25% to about 100% of the surface area of the core is covered by the film or films.

It is further noted that the visually distinct portions of the patterned film or films may be of different colors, hues, glosses, reflective qualities, brightness, depth, shades, chroma, opacity, etc. Patterned films may also be embossed or etched with surface relief patterns for textural and visual effects, as in the case of a holographic image or pattern. For example, the patterned film could have at least two portions having different visual appearances as follows: a red portion and a yellow portion (such as red and yellow stripes, or a red background having yellow spots thereon), or a flat finish portion and a glossy portion, or an opaque portion and a translucent portion. While the apparatus and methods of the present invention will be discussed hereinafter as employing films that have differently colored stripes (i.e., red and yellow stripes) with a color transition line therebetween, it will be understood that the patterned films may have any of the foregoing types of visually distinct portions, or combinations thereof, including visual distinctions not specifically mentioned herein.

It is further noted that the films of the present invention may be made of any elastic, plastic material (i.e., stock film forming material) that is preferably pharmaceutically acceptable and which is, or can be made, semi-liquid and flowable to facilitate the formation of a patterned, seamless and continuous film that can be made formable and malleable and which has smooth and controllable transition lines between the visually distinct portions thereof. More particularly, the films of the present invention may be formed of various materials, including, but not limited to, compositions comprising, consisting of, and/or consisting essentially of a film former; optionally a thickener; optionally an extender, optionally a plasticizer, and optionally various adjuvants and excipients.

Any film former known in the art is suitable for use in film composition of the present invention. Examples of suitable film forming materials include, but are not limited to, cellulosics such as methylcellulose, hydroxypropylcellulose (HPC), hydroxyethylmethylcellulose (HEMC), hydroxypropylmethylcellulose (HPMC), hydroxybutylmethylcellulose (HBMC), hydroxyethylethylcellulose (HEEC), and hydroxyethylhydroxypropylmethyl cellulose (HEMPMC); modified starches such as cross-linked starches, chemically modified starches including hydroxypropyl starch, hydroxyethyl starch, methylethyl starch, carboxymethyl starch; and physically modified starches including pre-gelatinized starches; proteins such as gelatin, whey protein, egg albumin, casein and casein isolates, soy protein and soy protein isolates; and other film-forming polymers such as polyvinylalcohol (PVA), methacrylic acid and methacrylate ester copolymers, polyvinyl alcohol and polyethylene glycol copolymers, and derivatives and mixtures thereof.

One suitable hydroxypropylmethylcellulose compound is "HPMC 2910", which is a cellulose ether having a degree of substitution of about 1.9 and a hydroxypropyl molar substitution of 0.23, and containing, based upon the total weight of the compound, from about 29% to about 30% methoxyl and from about 7% to about 12% hydroxylpropyl groups. HPMC 2910 is commercially available from the Dow Chemical Company under the tradename, "METHOCEL E." "METHOCEL E5," which is one grade of HPMC-2910 suitable for use in the present invention, has a viscosity of about 4 to 6 cps (4 to 6 millipascal-seconds) at 20 degrees Celsius in a 2% aqueous solution as determined by a Ubbelohde viscometer. Similarly, "METHOCEL E6," which is another grade of HPMC-2910 suitable for use in the present invention, has a viscosity of about 5 to 7 cps (i.e., 5 to 7 millipascal-seconds) at 20 degrees Celsius in a 2% aqueous solution as determined by a Ubbelohde viscometer. "METHOCEL E15," which is another grade of HPMC-2910 suitable for use in the present invention, has a viscosity of about 15000 cps (15 millipascal-seconds) at 20 degrees Celsius in a 2% aqueous solution as determined by a Ubbelohde viscometer. As used herein, "degree of substitution" shall mean the average number of substituent groups attached to a anhydroglucose ring, and "hydroxypropyl molar substitution" shall mean the number of moles of hydroxypropyl per mole anhydroglucose.

One suitable polyvinyl alcohol and polyethylene glycol copolymer is commercially available from BASF Corporation under the tradename "KOLLICOAT IR".

As used herein, "modified starches" include starches that have been modified by crosslinking, chemically modified for improved stability or optimized performance, or physically modified for improved solubility properties or optimized performance. Chemically modified starches have typically been treated with chemicals so that some hydroxyl groups have been replaced by either ester or ether groups. Very low levels of chemical modification can significantly change the rheological, physical, and chemical properties of starch. Crosslinking, in which two hydroxyl groups on neighboring starch molecules are linked chemically is also a form of chemical modification. As used herein, "pre-gelatinized starches" or "instantized starches" refers to physically modified starches that have been pre-wetted, then dried to enhance their cold-water solubility. Acid-hydrolyzed starch is a term used for a starch suspension treated with dilute acid at a temperature below the gelatinization point. The granular form of the starch is maintained and the reaction is ended by neutralization, filtration and drying once the desired degree of conversion is reached. This results in a reduction in the average molecular size of the starch polymers. Acid-hydrolyzed starches tend to have a lower hot viscosity than native starch and a strong tendency to gel when cooled. Suitable modified starches are commercially available from several suppliers such as, for example, A.E. Staley Manufacturing Company, and National Starch & Chemical Company.

One suitable modified starch includes the pre-gelatinized waxy maize derivative starches that are commercially available from National Starch & Chemical Company under the tradenames, "PURITY GUM" and "FILMSET", and derivatives, copolymers, and mixtures thereof. Such waxy maize starches typically contain, based upon the total weight of the starch, from about 0% to about 18% of amylose and from about 100% to about 88% of amylopectin.

Another suitable modified starch includes the hydroxypropylated starches. These are starches in which some of the hydroxyl groups have been etherified with hydroxypropyl groups, usually by treatment with propylene oxide. These starches are characterized by having excellent refrigeration and freeze/thaw stability. Hydroxypropyl food starches are generally crosslinked in addition to the etherification. Hydroxypropyl distarch phosphate is a starch used widely in the food industry in which both monofunctional hydroxypropyl groups have been added in combination with phosphate crosslinking. One example of a suitable hydroxypropyl starch is commercially available from Grain Processing Company under the tradename, "PURE-COTE B790".

Suitable tapioca dextrins include those available from National Starch & Chemical Company under the tradenames "CRYSTAL GUM" or "K-4484", and derivatives thereof such as modified food starch derived from tapioca, which is available from National Starch and Chemical Company under the tradename "PURITY GUM 40", and copolymers and mixtures thereof.

Any thickener known in the art is suitable for use in the film composition of the present invention. Examples of such thickeners include but are not limited to hydrocolloids such as alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, whelan, rhamsan, zooglan, methylan, chitin, cyclodextrin, chitosan, clays, acid hydrolyzed starches and derivatives and mixtures thereof. Additional suitable thickeners include sucrose, dextrose, fructose, and the like, and derivatives and combinations thereof.

Suitable xanthan gums include those available from C.P. Kelco Company under the tradename, "KELTROL 1000," "XANTROL 180," or "K9B310."

Suitable clays include smectites such as bentonite, kaolin, and laponite; magnesium trisilicate, magnesium aluminum silicate, and the like, and derivatives and mixtures thereof. The smectites are a group of minerals that swell as they absorb water or organic molecules within the structural layers; they also have considerable cationic exchange properties.

Suitable acid hydrolyzed starches include that commercially available from Grain Processing Corporation under the tradename, "PURE-SET B950", and hydroxypropyl distarch phosphates such as that commercially available from Grain Processing Corporation under the tradename, "PURE-GEL B990".

Suitable extenders include malotdextrin and polydextrose and mixtures and derivatives thereof.

Any plasticizer known in the pharmaceutical art is suitable for use in the present invention, and may include, but not be limited to polyethylene glycol; glycerin; sugar alcohols; triethyl citrate; tribuyl citrate; dibutyl sebecate; vegetable oils such as castor oil; surfactants such as polysorbates, sodium lauryl sulfates, and dioctyl-sodium sulfosuccinates; propylene glycol; mono acetate of glycerol; diacetate of glycerol; triacetate of glycerol; natural gums and mixtures thereof.

Suitable sugar-alcohols include sorbitol, mannitol, xylitol, maltitol, erythritol, lactitol, and mixtures thereof. In solutions containing a cellulose ether film former, an optional plasticizer may be present in an amount, based upon the total weight of the solution, from about 0% to about 40%.

Other suitable film materials include the gelatin-based material disclosed in U.S. Pat. Nos. 5,146,730 and 5,459,983, as well as other materials discussed therein that include, but are not limited to, polymers, such as polyvinyl chloride and polyvinyl pyrrolidone.

In one embodiment, the film composition contains, based upon the total dry solids weight of the composition, from about 95% to less than about 100%, e.g. from about 95% to about 99.5%, of a film former such as a cellulose ether, e.g., hydroxypropylmethylcellulose; and optionally from about 0.5% to about 5% of a thickener such as a hydrocolloid, e.g., xanthan gum; and optionally, from about 0.1% to about 1.0%, e.g. from about 0.25% to about 0.5% of a plasticizer such as vegetable oils, e.g. castor oil.

In an embodiment wherein the film forming agent is a thermoplastic starch, the film composition may include from about 60% to about 90% thermoplastic starch, about 0.5% to about 10% plasticizers, about 0% to about 40% hydrophilic extenders such as gelatin and about 0% to about 5% release aids such as fats or waxes. The formulation of such embodiments is described in further detail in U.S. Pat. Nos. 5,427,614 and 4,673,438. The portions of U.S. Pat. Nos. 5,427,614 and 4,673,438 which disclose the formulations and the methods of producing such formulations are hereby incorporated herein by reference.

In another embodiment, wherein the film forming agent is a cellulose either, such as hydroxypropylmethylcellulose (HPMC), the film composition may include about 70% to about 90% hydroxypropylmethylcellulose (HPMC), about 5% to about 20% plasticizers, such as glycerine or polyethylene glycol, about 0.5% to about 2.5% water and about 1% to about 20% hydrophilic extenders such as gelatin. The formulation of such embodiments is described in further detail in U.S. Pat. Nos. 4,655,840 and 4,790,881. The portions of U.S. Pat. Nos. 4,655,840 and 4,790,881 which disclose the formulations and the methods of producing such formulations are hereby incorporated herein by reference.

In a further embodiment, wherein the film forming agent is a chemically modified starch, the thickener may be selected from the group consisting of kappa or iota carrageenan, maltodextrin, gellan gum, agar, thin boiling starch, hydroxypropyl distarch phosphate and derivatives and mixtures thereof.

In another embodiment, wherein the film forming agent is a chemically modified starch, the plasticizer may be selected from the group consisting of glycerin, propylene glycol, polyethylene glycol, sugar alcohols and derivatives and mixtures thereof.

Optionally, the composition may further comprise other ingredients such as, based upon the total weight of the formulation, from about 0% to about 2% preservatives such as methylparaben and propylparaben, from about 0% to about 14% opacifying agents such as titanium dioxide, and/or from about 0% to about 14% colorants. See Remington's Practice of Pharmacy, Martin & Cook, 17$^{th}$ ed., pp. 1625-30, which is herein incorporated by reference.

Any coloring agent suitable for use in pharmaceutical applications may be used in the present invention and may include, but not be limited to azo dyes, quinopthalone dyes, triphenylmethane dyes, xanthene dyes, indigoid dyes, iron oxides, iron hydroxides, titanium dioxide, natural dyes, and mixtures thereof. More specifically, suitable colorants include, but are not limited to patent blue V, acid brilliant green BS, red 2G, azorubine, ponceau 4R, amaranth, D&C red 33, D+C red 22, D+C red 26, D+C red 28, D+C yellow 10, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanins, turmeric, cochineal extract, clorophyllin, canthazanthin, caramel, betanin, and mixtures thereof.

In one embodiment, the dosage form is comprised of a) a core; b) an optional first coating layer comprised of a subcoating that substantially covers the core; and c) a second coating layer on the surface of the first coating layer, the second coating layer comprised of the coating composition of the present invention. As used herein, "substantially covers" shall mean at least about 95% of the surface area of the core is covered by the subcoating. In a preferred embodiment the core contains a pharmaceutically active ingredient.

In an alternate embodiment, a first active ingredient may be contained in the first coating layer, and the core may contain a second active ingredient and/or an additional amount of the first active ingredient. In yet another embodiment, the active ingredient may be contained in the first coating layer, and the core may be substantially free, i.e., less than about 1%, e.g. less than about 0.1%, of active ingredient.

The use of subcoatings is well known in the art and disclosed in, for example, U.S. Pat. No. 3,185,626, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

The first embodiment of the present invention is directed to a novel rotary die apparatus and a method of enrobing cores using same. Initially, it is noted that, while various types of stock film forming materials are suitable for use in the embodiments described herein, gelatin-based materials are preferred.

U.S. Pat. Nos. 5,146,730 and 5,459,983 provide a complete and detailed description of the rotary die apparatus and method of enrobing cores to produce gelcaps suitable for use in the apparatus and method of the first embodiment. Accordingly, only those portions of the rotary die enrobing apparatus and process that are new and/or modified in accordance with the present invention will be described in full detail hereinafter.

Referring now to FIGS. 9-11, there are shown front (see FIG. 9), top (see FIG. 10) and side (see FIG. 11) representations of a film casting apparatus 30 used to produce a patterned film, more particularly a striped film 32, for enrobing cores 10 in accordance with the first embodiment of the present invention. More particularly, the film casting apparatus 30 includes film receiving means, such as a conventional casting drum 34 (see FIGS. 9 and 11), for receiving the film 32 cast thereon, as described in further detail hereinafter. The casting drum 34 rotates at a controllable rate in the direction indicated by the arrow B in FIG. 11. The casting drum 34 has an exterior surface 36, which may be polished and which may be cooled by conventional cooling means, such as circulating cooled water within the drum (not shown), for reasons discussed hereinafter.

With reference now, in particular, to FIGS. 10 and 11, the film casting apparatus 30 further includes film depositing means, such as a multi-chamber slit extruder 38, for depositing the film 32 (see FIGS. 9-11) onto the casting drum 34. The film 32 is made of any stock film forming materials 40, 42 that are suitable for use in conjunction with the multi-chamber slit extruder 38. It is noted that FIG. 10 shows the film casting apparatus 30 as viewed from the top; and, therefore, it shows the interior 44 of the multi-chamber slit extruder 38. FIG. 11 shows the film casting apparatus 30 from the left side (i.e., looking in the direction of arrow A in FIG. 9), with the slit extruder 38 in partial cross section, such that the interior 44 thereof is partially visible. As shown in these figures, the slit extruder 38 has, generally, a floor panel 46 and four exterior walls 48, 50, 52, 54 (see FIG. 10), which define the interior 44 of the slit extruder 38. The slit extruder 38 also includes flow control means, such as a slidable gate 56 (see FIG. 11), for a purpose to be described hereinafter. Three partitions 58, 60, 62 divide the interior 44 of the slit extruder 38 into four chambers 64, 66, 68, 70. In this regard, it is noted that the slit extruder 38 may include more or fewer partitions than are shown in the present embodiment resulting in more or fewer chambers, respectively, than are shown in the present embodiment. The film casting apparatus 30 also includes supply means, such as feeder pipes 72, 74 (shown in partial cross section in FIGS. 9-11 to reveal the stock film forming materials 40, 42 flowing therethrough) for supplying stock film forming materials 40, 42 to the chambers 64, 66, 68, 70 in a manner to be described hereinafter.

As can be seen best in FIG. 11, one of the exterior walls 48 of the slit extruder 38 may have an inner surface 76 that is sloped toward the floor panel 46 and terminates proximate thereto, thus forming an open slit 78 between the bottommost portion of the wall 48 and the floor panel 46. The open slit 78 communicates with each of the chambers 64, 66, 68, 70 of the slit extruder 38 to allow passage therethrough of the stock film forming materials 40, 42. The slit extruder 38 is heated by conventional heating means, such as electric coils, or coils with hot water circulating therein (not shown), for the purpose of heating the stock film forming materials 40, 42 to (or maintaining the stock film forming materials 40, 42 at) a flowable liquid state, such that the stock film forming materials 40, 42 will flow through the slit 78 and out of the chambers 64, 66, 68, 70 in a manner to be described hereinafter. The width of the slit 78, and, hence, the thickness of the resulting film 32, is adjusted by moving the slidable gate 56 in the directions indicated by arrow C in FIG. 11.

The slit extruder 38 may also include a top cover 80 (see FIGS. 9 and 11) to facilitate pressurizing the interior 44 of the slit extruder 38 by conventional pressurizing means (not shown), which will encourage the stock film forming materials 40, 42 to flow out of the chambers 64, 66, 68, 70 in a manner to be described hereinafter. As a further optional feature, the slit extruder 38 may include an interior roller 82 (see FIG. 11), which is adapted to rotate in the direction indicated by the arrow D so as to encourage the stock film forming materials 40, 42 to flow out of the chambers 64, 66, 68, 70 in a manner to be described hereinafter.

As shown in FIGS. 9-11, when the chambers 64, 66, 68, 70 of the slit extruder 38 contain differently colored stock film forming materials 40, 42 in alternating chambers 64, 66, 68, 70 (e.g., "red" stock material 40 in the chambers 64, 68 and "yellow" stock material 42 in the chambers 66, 70), the resulting film 32 will have differently colored stripes (i.e., red stripes 84, 88 and yellow stripes 86, 90). In addition, where the slit extruder 38 includes more or fewer chambers than are shown in FIGS. 9-11, the resulting striped film 32 will have more or fewer stripes, respectively, than the film 32 shown in the present embodiment.

It is noted that, of course, the stock film forming materials 40, 42 need not be of different colors, but rather, they can be visually distinct from one another by having, for example, different colors, hues, glosses, reflective qualities, brightness, depth, shades, chroma, opacity, etc. Red and yellow stock film forming materials 40, 42, respectively, are discussed herein merely by way of example and, it should be understood that stock film forming materials that are visually distinct from one another in other ways, as mentioned above, are also suitable for use with the apparatus and method of the present invention. Furthermore, stock film forming materials 40, 42 of more than two different colors (for example, four stock materials of four different colors), or other visual distinctions (such as, for example, a first flat stock material, a second glossy stock material and a third stock material having reflective qualities), may also be used. It is further noted that the stock film forming materials 40, 42 may be of different chemical compositions (i.e., they need not both be made of polymer or starch-based materials, or even of the same polymer or starch-based formulation) and still be suitable for use with the apparatus and methods of the present invention as long as the stock film-forming materials are sufficiently compatible with one another such that they will form a continuous patterned film by the methods described hereinafter.

Figure 12:
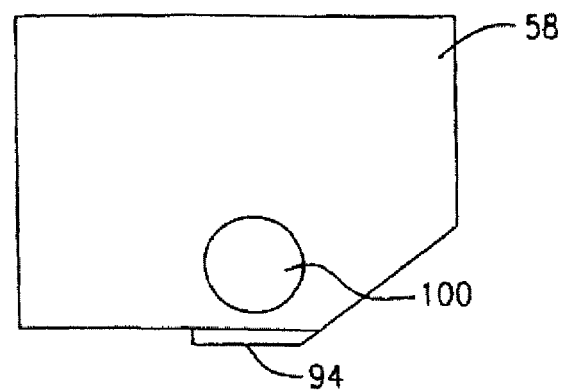
FIG. 12 is an elevational left side view of one of the partitions that is positioned within the slit extruder.
Figure 13:
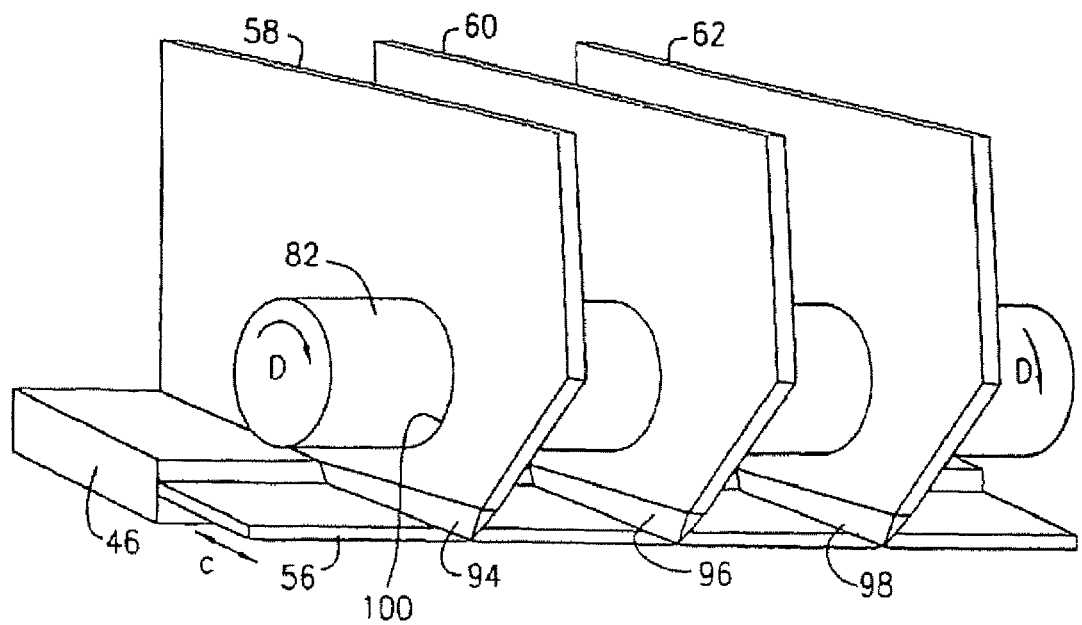
FIG. 13 is a perspective view of the interior roller, partitions and slidable gate of the slit extruder of FIGS. 9-11.

With reference now to FIGS. 12 and 13, to ensure that the color transitions 92a, 92b, 92c between stripes 84, 86, 88, 90 of different colors (or visual distinction) in the film 32 are straight and consistent (see, e.g., FIG. 9), the slit extruder 38 includes a stripe control means, such as a tapered blade edge 94, 96, 98 on each partition 58, 60, 62, respectively, to control the flow of the stock film forming materials 40, 42 as they exit the chambers 64, 66, 68, 70. FIG. 12 shows a single isolated partition 58, removed from the slit extruder 38 and having a tapered blade edge 94, as well as a hole 100 that is sized and shaped to rotatably receive the interior roller 82 therethrough. As shown in FIG. 13, when the partitions 58, 62, 62 and the interior roller 82 are properly installed within the slit extruder 38, the tapered edge 94, 96, 98 of each partition 58, 60, 62, respectively, rests upon the floor panel 46 and extends across the slit 78.

The operation of the film casting apparatus 38, by which striped film 32 is produced, will now be described in detail using FIGS. 9-13 as references. Initially, one feeder pipe 72 supplies the stock film forming material 40 of one color (or visual distinction), such as red, to two alternate chambers 64, 68 of the slit extruder 38, while the other feeder pipe 74 supplies stock film forming material 42 of another color (or visual distinction), such as yellow, to the remaining two chambers 66, 70. The stock film forming materials 40, 42 may be provided to the extruder 38 in the form of liquid, a solid, or a semi-solid, and may be at any desired temperature. A conventional heating means (not shown) of the slit extruder 38 may be activated, thereby heating the stock film forming materials 40, 42 within the chambers 64, 66, 68, 70 to a predetermined temperature (or maintaining the stock film forming materials 40, 42 at such a temperature), at which the stock film forming materials 40, 42 become liquid and flowable or may be maintained in a liquid and flowable state. Depending upon the type and composition of the stock film forming materials 40, 42, it may be exposed to a temperature between about 40 degrees Celsius and about 250 degrees Celsius. For example, where the stock film forming materials 40, 42 are gelatin based or hydroxypropyl methylcellulose based, then the appropriate temperature range for heating within the slit extruder 38 would be between about 40 degrees Celsius and about 190 degrees Celsius. Alternatively, where the stock film forming materials 40, 42 are starch based, then the appropriate temperature range for heating within the slit extruder 38 would be between about 80 degrees Celsius and about 240 degrees Celsius.

According to known, conventional processes, the rotation of the casting drum 34 is commenced and the exterior surface 36 of the casting drum 34 is cooled by conventional cooling means (not shown) to a predetermined temperature that will, at least partially, solidify the stock film forming materials 40, 42 upon their physical contact with the surface 36 of the drum 34 to form the striped film 32, as described in further detail hereinafter. One skilled in the art would readily appreciate, without undue experimentation, the proper predetermined temperature for the exterior surface 36 of the drum 34 will depend upon several factors such as, for example, the type and composition of the stock film forming materials 40, 42 and the desired thickness of the resulting film 32. For example, where the stock film forming materials 40, 42 are gelatin based or hydroxypropyl methylcellulose based, and the desired film thickness is about 0.1 millimeters to about 2.0 millimeters, then the appropriate temperature range for cooling the exterior surface 36 of the casting drum 34 would be between about 2 degrees Celsius and about 50 degrees Celsius. Alternatively, where the stock film forming materials 40, 42 are thermoplastic starch based, and the desired film thickness is about 0.1 millimeters and about 2.0 millimeters, then the appropriate temperature range for cooling the surface 36 of the drum 34 would be between about 20 degrees Celsius and about 100 degrees Celsius.

After the stock film forming materials 40, 42 are heated to, or maintained at, the appropriate predetermined temperature and the exterior surface 36 of the casting drum 34 is cooled to the appropriate predetermined temperature, the slidable gate 56 of the slit extruder 38 is moved to a position which opens the slit 78 to the thickness that is desired for the film 32. The stock film forming materials 40, 42 then flow out of their respective chambers 64, 66, 68, 70, along the tapered blade edges 94, 96, 98, through the slit 78, and onto the casting drum 34, in a controlled manner, in the direction of the arrow E in FIG. 9. The aforesaid apparatus and procedure result in the production of a continuous ribbon of striped film 32, having alternating red stripes 84, 88 and yellow stripes 86, 90, with straight and consistent color transitions 92a, 92b, 92c therebetween. The film 32 is continuously removed from the casting drum 34 by a scraper or similar device (not shown).

Figure 14:
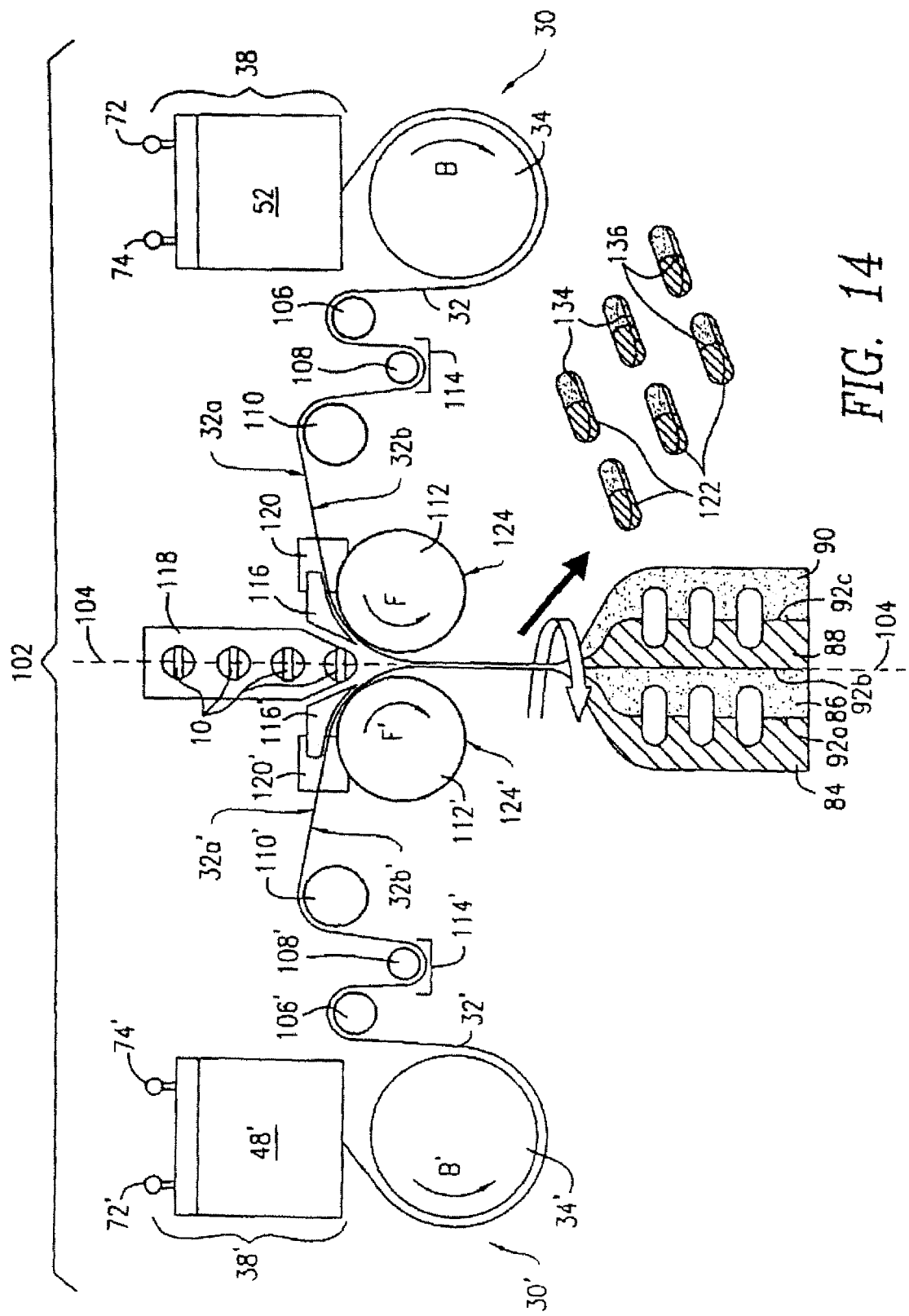
FIG. 14 is a simplified, schematic elevational front view of the enrobing apparatus, including the film-casting apparatus of FIGS. 9-13, in accordance with the first embodiment of the present invention.
Figure 15:
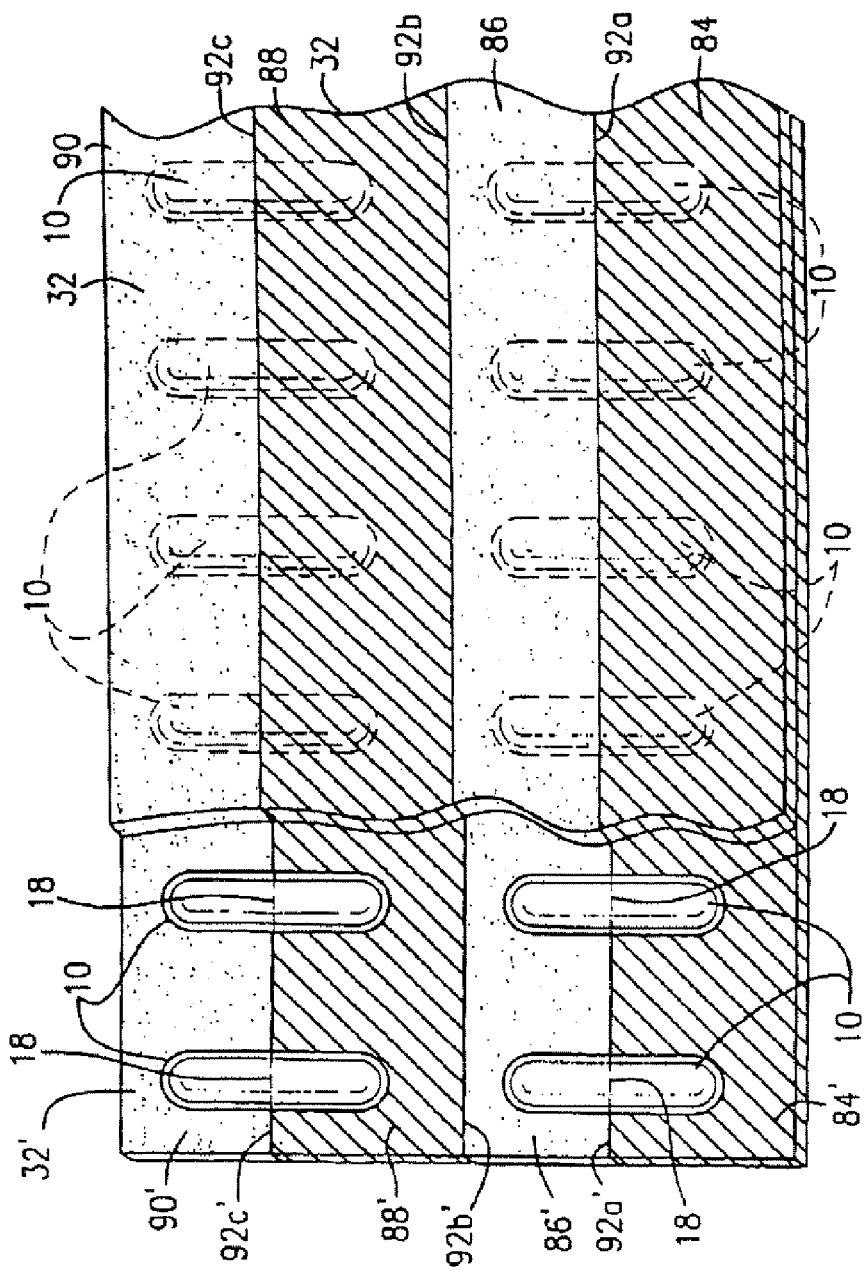
FIG. 15 is a top plan view of a portion of two overlapped striped films with cores placed therebetween, showing the proper orientation of the cores in relation to the stripes on the films.
Figure 16:
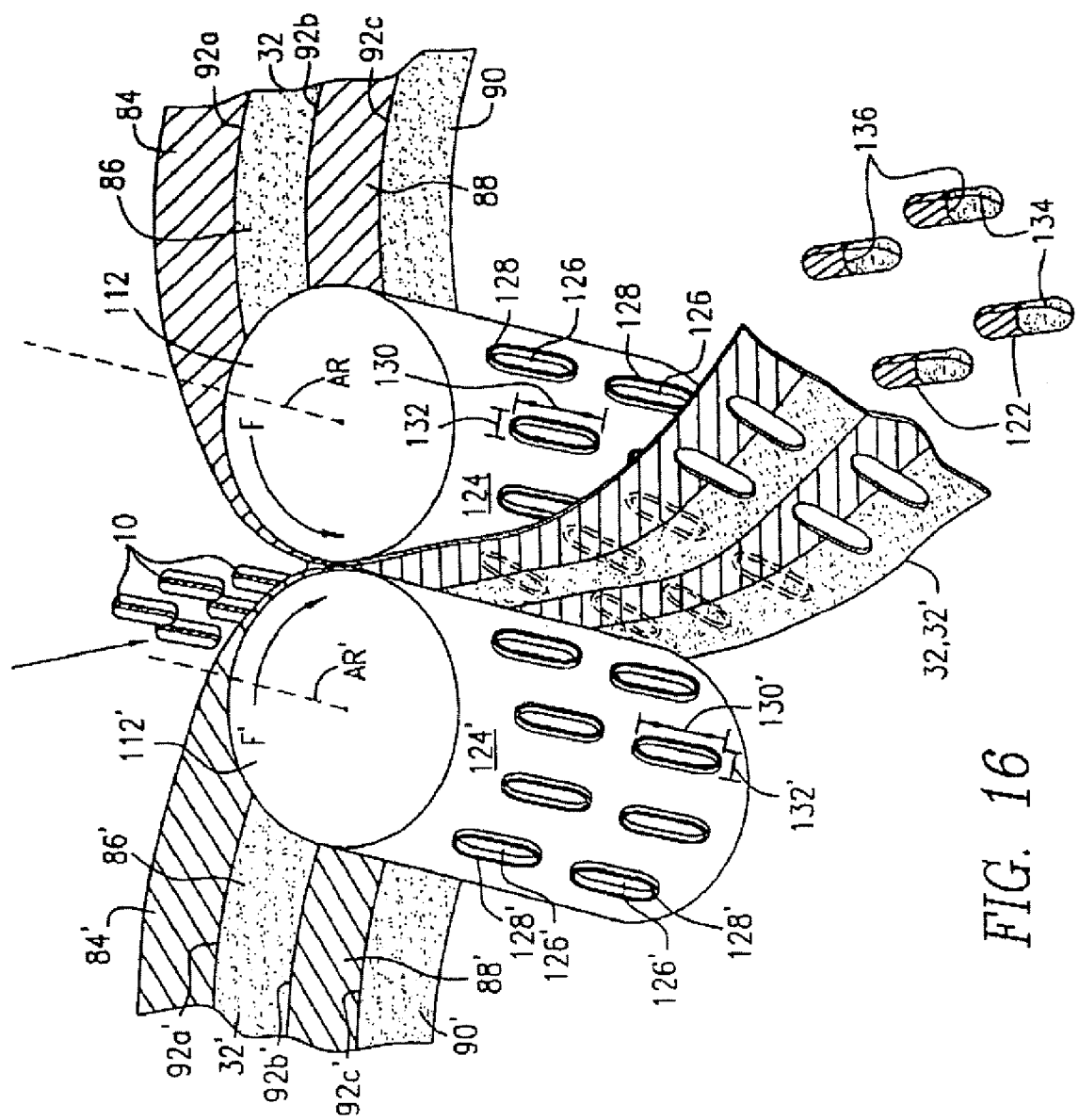
FIG. 16 is a simplified perspective view of the rotating die and striped films, as well as enrobed cores produced thereby, in accordance with the first embodiment of the present invention.

With reference now to FIGS. 14-16, a summary of the enrobing apparatus 102 (see FIG. 14) in accordance with the first embodiment of the present invention will now be provided. Reference is also made to U.S. Pat. Nos. 5,146,730 and 5,459,983, which both provide a detailed description of the enrobing apparatus 102.

With reference in particular to FIG. 14, it is noted that the enrobing apparatus 102 has a central plane of symmetry 104 about which the various equipment that comprises the enrobing apparatus 102 are arranged. As depicted schematically in FIG. 14, it can be seen that the equipment of the enrobing apparatus 102 on one side of the central plane of symmetry 104 is basically the same type as the equipment on the other side of the central plane of symmetry 104 and is arranged, generally, in a mirror image thereof. More particularly, a film casting apparatus 30, 30' is positioned at each of the opposite ends of the enrobing apparatus 102 and each film casting apparatus 30, 30' produces a striped film 32, 32', respectively. Each film 32, 32' is moved in a continuous manner, by a series of rollers 106, 108, 110, and 106', 108', 110', respectively, toward a pair of coacting rotary dies 112, 112', which are positioned symmetrically on either side of the central plane of symmetry 104. The rotary dies 112, 112' rotate on their axes of rotation AR, AR', respectively, in the directions of arrows F, F', respectively, thereby forming a nip therebetween. The nip between the rotary dies 112, 112' lies in the aforesaid central plane of symmetry 104 and the striped films 32, 32' are passed therethrough.

Each film 32, 32' includes a top or contact surface 32a, 32a' and a reverse surface 32b, 32b', respectively (see FIG. 14). Shortly after the striped films 32, 32' are cast and removed from the cooled casting drums 34, 34', as described earlier hereinabove, the reverse surface 32b, 32b' of each film 32, 32' may be lubricated in a lubricant bath 114, 114' to facilitate their movement over the rollers 106, 108, 110, 106', 108', 110'. Suitable lubricants include any fats or oils, which are well-known in the art for such use. Just prior to the passage of the films 32, 32' into the nip between the rotary dies 112, 112', the contact surface 32a, 32a' of each of the films 32, 32' may be heated by conventional heating means 116, 116' to facilitate their bonding to one another as they pass between the rotary dies 112, 112'.

The enrobing apparatus 102 also includes a core dispensing means 118, which holds a supply of cores 10 and dispenses them to the nip between the rotary dies 112, 112' in a timed manner. Although this embodiment is illustrated as enrobing cores, it is within the scope of the present invention to alternatively enrobe any substrate with a desired film coating, including but not limited to a hard or soft capsules, gels, lozenges, nougats, fondants, etc., or other confectionery. The core dispensing means 118 is aligned with the central plane of symmetry 104 and the nip formed between the rotary dies 112, 112'. The core dispensing means 118 orients and dispenses each core 10 such that the core 10 simultaneously contacts the contact surfaces 32a, 32a' of the converging striped films 32, 32' as the core 10 enters the nip between the dies 112, 112', with its transverse plane of symmetry 16 lying in the central plane of symmetry 104 of the enrobing apparatus 102, and the color transitions 92a, 92a' of the films 32, 32', respectively, lying in the conjugate plane of symmetry 18 of the core 10. The films 32, 32' are then stretched around the opposite sides of each core 10 symmetrically, relative to the central plane of symmetry 104 of the enrobing apparatus 102.

FIG. 15 shows the proper positioning of the cores 10 in between the striped films 32, 32' as they enter the nip between the dies 112, 112' and relative to the color transitions 92a, 92b, 92c, 92a', 92b', 92c' of each film 32, 32'. In FIG. 15, the first film 32 is partially cut away to show the cores 10 placed on the second film 32'. The cores 10 that are shown in phantom in FIG. 15 are sandwiched in between the films 32, 32', thereby showing how the color transitions 92a, 92b, 92c of the first film 32 align with the color transitions 92a', 92b', 92c' of the second film 32', respectively, and how all of the color transitions 92a, 92b, 92c, 92a', 92b', 92c' are aligned with the conjugate plane of symmetry 16 (not shown on the phantom cores 10) of a corresponding core 10.

Furthermore, the enrobing apparatus 102 preferably includes registering means 120 (shown only schematically in FIG. 14) for ensuring that the colored stripes (not shown) of the films 32, 32' are properly aligned with one another prior to passage between the rotary dies 112, 112'. The registering means 120 also ensures that the positions of the dispensed cores 10 are appropriate relative to the color transitions 92a, 92b, 92c, 92a', 92b', 92c' of the films 32, 32', respectively, such that the color transition between the colors on the resulting gelcap products 122 are properly matched with one another and the conjugate plane of symmetry 18 of each core 10. More particularly, the registering means 120 (shown schematically only in FIG. 14) may include any one of many any other conventional, known types of optical sensory and control devices (commercially available from Contrex, Inc. of Maple Grove, Minn. and Ormec Systems Corp. of Rochester, N.Y.), as well as any other conventional, known mechanical adjusting means for adjusting the position of one or both of the films 32, 32', as necessary.

With reference now to FIG. 16, an enlarged schematic perspective view of the drum-like rotary dies 112, 112' is provided. As shown, the rotary dies 112, 112' are substantially identical to one another, each having an exterior circumferential surface 124, 124' with a series of recesses 126, 126' thereon. The recesses 126, 126' are arranged in rows, which extend circumferentially around each rotary die 112, 112'. Furthermore, each recess 126, 126' has a raised rim 128, 128' about its periphery for a purpose to be described hereinafter. It is noted that, as shown in FIG. 16, each recess 126, 126' is shaped to conform to the shape of the cores 10 being enrobed. More particularly, for purposes of the present illustration wherein oblong cores 10 are being enrobed, each recess 126, 126' has a length 130, 130' and a width 132, 132' and each is arranged such that its length 130, 130' is aligned parallel to the axis of rotation AR, AR' of its respective rotary die 112, 112'. In addition, it is contemplated that each die 112, 112' may have a different number of rows of recesses 126, 126' than are shown in the present embodiment, as long as there are the same number of rows on each die 112, 112' so that each recess 126 on one die 112 can cooperate with a corresponding recess 126' on the other die 112', as described in further detail hereinafter. In addition, the number of rows of recesses 126, 126' should correspond to the number of color transitions 92a, 92b, 92c, 92a', 92b', 92c' between the stripes 84, 86, 88, 90, 84', 86', 88', 90' on the striped films 32, 32', respectively, that pass between the dies 112, 112', for reasons which will be apparent based upon the operation of the enrobing apparatus 102 described hereinafter. The dies 112, 112' should be at or below room temperature and may be brought to, or maintained at, such temperature by any suitable conventional, known temperature control means (not shown). In addition, if desired, the exterior circumferential surfaces 124, 124', including the recesses 126, 126', of each die 112, 112', respectively, may be treated so as to reduce the tendency of the films 32, 32' to stick thereto, such as, for example, applying a suitable conventional lubricant thereto, or coating the surfaces 124, 124' with TEFLON® or anodizing the surfaces 124, 124'.

As can be seen in FIG. 16, the orientation of the striped films 32, 32' as they pass between the rotary dies 112, 112' is such that the red stripes 84, 88 of one film 32 are matched with the red stripes 84', 88' of the other film 32' and the yellow stripes 86, 90, 86', 90' of each film 32, 32', respectively, are similarly matched with one another. The registering means 120 of the enrobing apparatus 102 may be used to facilitate the orientation of the films 32, 32' such that the matching and alignment of the color transitions 92a, 92b, 92c, 92a', 92b', 92c' of each film 32, 32', respectively, are improved.

As the dies 112, 112' rotate, each recess 126 of one rotary die 112 cooperates with a corresponding recess 126' on the other rotary die 112' at the nip between the dies 112, 112' to form a cavity therebetween. The recesses 126, 126' are sized and shaped such that the cavities formed therebetween are slightly larger than the enrobed core 10, thereby preventing unnecessary contact between the films 32, 32' and the interior surfaces of the recesses 126, 126'. As the rotary dies 112, 112' rotate, the cores 10 are dispensed to the nip between the dies 112, 112' such that they are oriented with their lengths aligned parallel to the axes of rotation AR, AR' of the dies 112, 112' and each core 10 is thereby properly aligned to be received between a pair of coacting recesses 126, 126'. The rotary dies 112, 112' continue to rotate and the films 32, 32' are sealed to each other by the raised rims 128, 128' of the coacting recesses 126, 126', around the core 10 thereby forming a film seam 134, which lies in the transverse plane of symmetry 16 of the core 10. The raised rims 128, 128' also cut through the bonded films 32, 32', at the film seam 134 around each enrobed core 10, thereby releasing the enrobed core products, or gelcaps 122, from the bonded films 32, 32'.

With reference to the film seam 134 of the gelcaps 122, it is noted that in addition to the configuration described above wherein the films 32, 32' are sealed together and cut by the raised rims 128, 128' of the coacting recesses 126, 126' thereby resulting in abutting film edges that form the film seam 134, it is also possible to have a film seam 134 wherein the cut edge of one film 32 slightly overlaps the cut edge of the other film 32' by an amount approximately equal to the thickness of the films 32, 32'. Alternatively, the film seam 134 could be formed such that the cut edges of the films 32, 32' are aligned with one another about the core 10, but are spaced apart slightly by a distance that is approximately equal to the thickness of the films 32, 32'. Regardless of which of the foregoing types of film seams 134 (i.e., abutting, overlapping or spaced apart) that is formed on the gelcap product 122, the film seam 134 lies substantially in the transverse plane of symmetry 16 of the core 10. It should be understood that the foregoing discussion of the possible types of film seams also applies to all embodiments of the present invention discussed hereinafter.

As shown in FIGS. 14 and 16, the film coatings of the resulting gelcaps 122 conform tightly and snugly to the cores 10, thereby resulting in tamper-proof gelcap products 122. In addition, the resulting gelcap product 122 is bi-colored, the film seam 134 lying in the transverse plane of symmetry 16 of the core 10 and the color transition 136 lying in the conjugate plane of symmetry 18 of the core 10. As a result, the color transition 136 of each of the gelcaps 122 may be flush and seamless (i.e., without any raised portion which generally characterizes the film seam 134). In addition, the foregoing process may result in gelcap products 122 having a film coating of uniform color quality and thickness over their entire surface.

If aesthetically desired, the films 32, 32' may be aligned such that the resulting gelcaps 122 have a film seam 134 wherein a stripe of one color (for example, a red stripe 84) (or visual distinction) of one film 32 abuts or overlaps a stripe of another color (for example, a yellow stripe 90') (or visual distinction) of the other film 32' to form a gelcap 122 having a "checkerboard pattern", i.e., having four quadrants of alternating red and yellow colors (or other visual distinctions) (not shown).

After being cut and released from the bonded films 32, 32' in a manner disclosed in U.S. Pat. Nos. 5,146,730 and 5,459, 983, the gelcaps 122 may be collected in collecting chutes and/or conveyors (not shown) and transported to further processing equipment (not shown) for further process steps in which the lubricants may be removed, the gelcaps 122 may be dried and/or, if desired, additional coatings or identifying markings may be added.

As illustrated in FIGS. 17-21, the second embodiment of the present invention is directed to an alternative method for producing striped film having transversely oriented stripes, using rotary die apparatus and process that are nearly identical to those described above.

Figure 18:
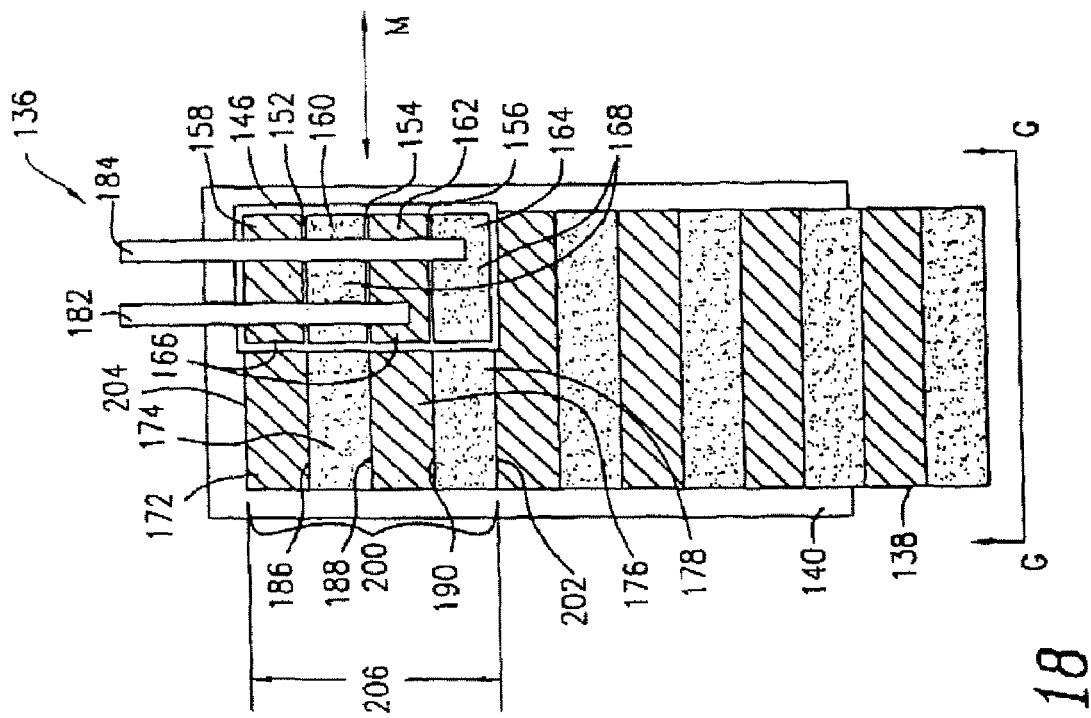
FIG. 18 is a simplified, schematic top plan view of the alternative film casting apparatus of FIG. 17, showing the interior chambers of the reciprocating slit extruder.
Figure 17:
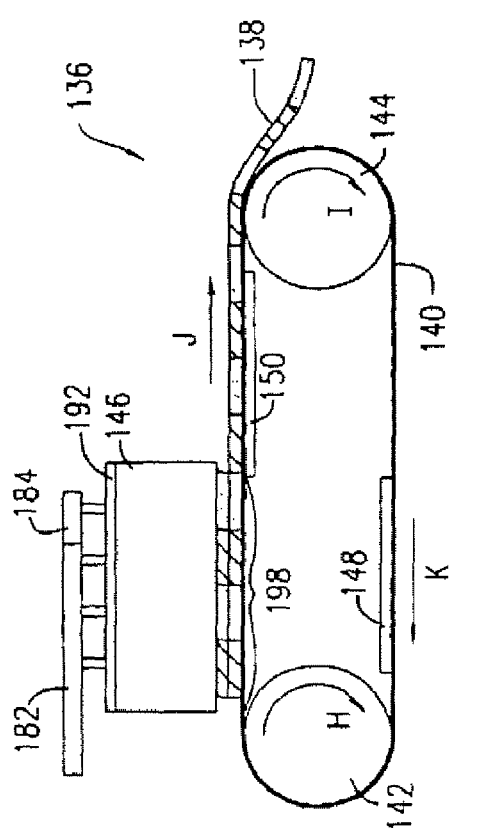
FIG. 17 is a simplified, schematic elevational side view of an alternative film casting apparatus in accordance with a second embodiment of the present invention.
Figure 19:
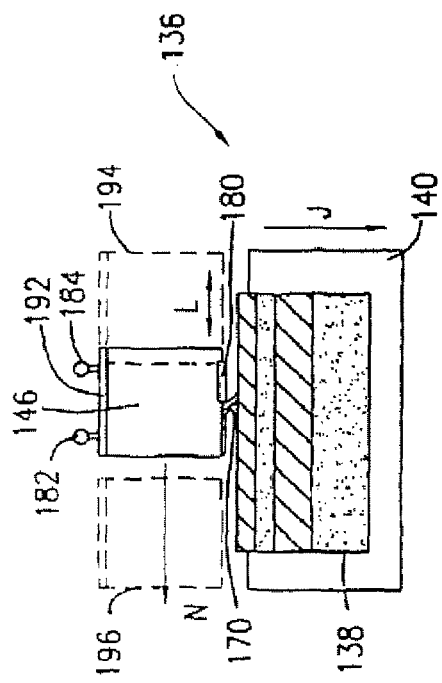
FIG. 19 a simplified, schematic elevational front view of the alternative film casting apparatus of FIG. 18, as viewed from the position of line G-G and looking in the direction of the arrows.

With reference particularly, to FIGS. 17-19, a simplified, schematic representation is provided of an alternative film casting apparatus 136, which produces the aforesaid transversely striped film 138 for enrobing cores 10 in accordance with the second embodiment of the present invention. More particularly, FIG. 17 shows an elevated side view of the alternative film casting apparatus 136, while FIG. 18 shows a top plan view thereof. FIG. 19 shows an elevated front view of the alternative film casting apparatus 136, as viewed from the position of line G-G in FIG. 18 and looking in the direction of the arrows.

Referring now to FIG. 17, the alternative film casting apparatus 136 includes film receiving means, such as a conventional metal casting belt 140 that is mounted onto two rotating drums 142, 144, for receiving the film 138 being cast thereon, as described in further detail hereinafter. The rotating drums 142, 144 rotate at a controllable rate in the directions indicated by the arrows H and I respectively, in FIG. 17, thereby causing the casting belt 140 to move in the directions indicated by the arrows J and K. While the casting belt 140 can be made of suitable materials other than metal that will removably receive the film 138 thereon, such as carbon steel or stainless steel available from Belt Technology of Agawam, Mass., metal is the preferred material. The surface of the casting belt 140 may be polished to reduce the tendency of the film 138 to stick thereon. In addition, a warming plate 148 may be positioned adjacent to the casting belt 140 to warm the casting belt 140 prior to casting film thereon, for a purpose discussed hereinafter. A cooling plate 150 is positioned adjacent to the casting belt 140 to cool the casting belt 140 after film is cast thereon, for a purpose that is also discussed hereinafter.

As shown in each of FIGS. 17-19, the alternative film casting apparatus 136 further includes film depositing means, such as a reciprocating multi-chamber slit extruder 146, for depositing the film 138, in a semi-continuous manner, as described hereinafter, onto the casting belt 138. Such extruders are conventional and well known to persons having ordinary skill in the art and are available commercially from various sources, including, but not limited to, Wenger Manufacturing of Kansas City, Mo. and Coperion Corporation of Ramsey, N.J. The configuration and operation of the slit extruder 146 are nearly identical to those of the slit extruder 38 of the first embodiment of the present invention. More particularly, as with the slit extruder 38 previously discussed hereinabove, the reciprocating slit extruder 146 includes interior partitions 152, 154, 156 that form interior chambers 158, 160, 162, 164 for holding visually distinct stock film forming material 166, 168 therein. As shown in FIG. 18, red stock film forming material 166 is held in chambers 158, 162 and yellow stock film forming material 168 is held in chambers 160, 164. A slit 170 is also provided, through which the stock film forming materials 166, 168 flow out of the chambers 158, 160, 162, 164 and onto the casting belt 140, thereby creating a striped film 138 as described hereinafter.

The reciprocating slit extruder 146 also includes supply means, such as feeder pipes 182, 184 for supplying the stock film forming materials 166, 168 to each of the chambers 158, 160, 162, 164 and flow control means, such as a slidable gate 180 (see FIG. 19), for controlling the flow of the stock film forming materials 166, 168 from the chambers 158, 160, 162, 164. The width of the slit 170 and, thereby, the thickness of the resulting film 138, is adjusted by moving the slidable gate 180 in the directions indicated by arrow L in FIG. 19. In addition, as with the slit extruder 38 previously discussed hereinabove, the reciprocating slit extruder 146 of the second embodiment may be heated by conventional heating means, such as electric coils, or coils with hot water circulating therein (not shown), for the purpose of heating the stock film forming materials 166, 168 to a flowable liquid state, (or maintaining the stock film forming materials 166, 168 at such state), such that the stock film forming materials 166, 168 will flow easily out of each chamber 158, 160, 162, 164 and through the slit 170.

Each of the interior partitions 152, 154, 156 of the reciprocating slit extruder 146 has stripe control means, such as a tapered blade edge (not shown, but similar to the tapered blade edges 94, 96, 98 of the partitions 58, 60, 62 shown in FIG. 13 in connection with the first embodiment), to control the flow of the stock film forming materials 166, 168 exiting the chambers 158, 160, 162, 164. As with the slit extruder 38 of the first embodiment, the tapered blade edges (not shown) of the interior partitions 152, 154, 156 of the reciprocating slit extruder 146 ensure the formation of straight and consistent color transitions 186, 188, 190 between the stripes of the film 138 as the film 138 is cast onto the casting belt 140.

Also similar to the slit extruder 38 of the first embodiment, the reciprocating slit extruder 146 may include a top cover 192 to facilitate pressurizing its interior, by conventional pressurizing means (not shown), thereby promoting the flow of the stock film forming materials 166, 168 out of the chambers 158, 160, 162, 164. Alternatively, the reciprocating slit extruder 146 may include a rotatable interior roller (not shown) positioned therein (see FIG. 11), which would also promote the flow of the stock film forming materials 166, 168 out of the chambers 158, 160, 162, 164.

With reference, in particular, to FIGS. 18 and 19, one notable difference between the slit extruder 38 of the first embodiment and the reciprocating slit extruder 146 of the second embodiment is that the reciprocating slit extruder 146 is connected to a conventional motor (not shown), in a manner that is known and familiar to those having ordinary skill in the art, such that it moves reciprocatingly in the directions indicated by arrow M in FIG. 18. For example, suitable reciprocating mechanisms are discussed in the following two books: Sclater and Chironis, *Mechanisms and Mechanical Devices Sourcebook*, Ch. 4 Reciprocating Mechanisms, McGraw-Hill Professional, June 2001 and Jones, et al., *Ingenious Mechanism*, Vol. 1 Driving Mechanisms for Reciprocating Parts, Industrial Press, November 1990, both of which are herein incorporated by reference.

More particularly, the reciprocating slit extruder 146 is movable between a first position 194 (shown in phantom in FIG. 19) and a second position 196 (also shown in phantom in FIG. 19), for a purpose described in detail hereinafter. Such movement of the reciprocating slit extruder 146 occurs at a constant speed and at timed intervals that are controlled and regulated by a combination of conventional motors (not shown) and registering means (not shown), such as those mentioned above in connection with the first embodiment of the present invention.

Other notable differences between the slit extruder 38 of the first embodiment and the reciprocating slit extruder 146 relate to the operation of the reciprocating slit extruder 146 and will become apparent from the following description. The operation of the alternative film casting apparatus 136, by which the transversely striped film 138 is produced, will now be described in detail, using FIGS. 17-19 as references.

Initially, the feeder pipes 182, 184 supply stock film forming materials 166, 168 of two colors, such as red and yellow, respectively, to alternate chambers 158, 160, 162, 164, respectively, of the reciprocating slit extruder 146. The conventional heating means (not shown) of the reciprocating slit extruder 146 is activated, thereby heating or maintaining the stock film forming materials 166, 168 within the chambers 158, 160, 162, 164 to a predetermined temperature, at which the stock film forming materials 166, 168 becomes or is maintained as liquid and flowable. The warming plate 148 may also be warmed to a predetermined temperature that is sufficient to maintain the aforesaid liquid and flowable characteristics of the stock material 166, 168 for a brief amount of time. The preferred temperatures for the stock material 166, 168 and the warming plate 148 are determined, based upon the type of stock material 166, 168 being used, in the same manner as described hereinabove in connection with the first embodiment of the present invention.

The cooling plate 150 is cooled by conventional cooling means (not shown) to a predetermined temperature that will, at least partially, solidify the stock material 166, 168 upon physical contact with the surface of the casting belt 140 to form the transversely striped film 138, as described in further detail hereinafter. One skilled in the art would readily appreciate, without undue experimentation, that the proper predetermined cooled temperature for the cooling plate 150 will depend upon a number of factors, including the type and composition of the stock film forming materials 166, 168 and the desired thickness of the transversely striped film 138, and may be determined in the same manner as described earlier hereinabove in connection with preferred temperature for the casting drum 34 of the first embodiment of the present invention.

After the stock film forming materials 166, 168, the warming plate 148 and the cooling plate 150 have attained their desired temperatures, a portion 198 of the casting belt 140 is warmed by the warming plate 148 and is then advanced by the rotating drums 142, 144 to a position underneath the reciprocating slit extruder 146. The slidable gate 180 is then moved to a position which opens the slit 170 to the thickness that is desired for the striped film 138. While the rotating drums 142, 144 and the casting belt 140 remain stationary, the stock film forming materials 166, 168 flow out of the chambers 158, 160, 162, 164, along the tapered blade edges (not shown), through the slit 170 and onto the warmed portion 198 of the casting belt 140, which briefly maintains the stock material 166, 168 in a substantially liquid, flowable state.

Simultaneously with the flow of the stock film forming materials 166, 168 onto the casting belt 140, the reciprocating slit extruder 146 is moved from its first position 194, at a constant predetermined speed, in the direction indicated by the arrow N in FIG. 19, to its second position 196, where it is temporarily halted. As soon as the reciprocating slit extruder 146 reaches its second position 196, the slidable gate 180 is moved to a closed position, thereby blocking the slit 170 and temporarily halting the flow of stock film forming materials 166, 168, which results in the formation of a film segment 200. As seen in FIG. 18, the film segment 200 has alternating, transversely oriented red stripes 172, 176 and yellow stripes 174, 178 with straight and consistent color transitions 186, 188, 190 therebetween. The film segment 200 also has a first edge 202, a second edge 204 and a width 206, which equals the sum of the widths of the stripes 172, 174, 176, 178.

Next, the casting belt 140 is moved by the rotating drums 142, 144 in the direction shown by arrows J and K in FIG. 17, such that the film segment 200 is moved in the direction of the arrow J and a newly warmed portion of the casting belt 140 is positioned beneath the reciprocating slit extruder 140. More particularly, the casting belt 140 is moved until the first and second edges 202, 204 of the film segment 200 are each advanced by a distance that is equal to the width 206 of the film segment 200, in order to make room for the casting of a second film segment that will be contiguous with the first film segment 200. It is noted that the cooling plate 150 is preferably positioned adjacent and beneath the casting belt 140 at the location to which the first film segment 200 is moved. Thus, the first film segment 200 is cooled while the second film segment is cast onto the casting belt 140. It will be appreciated by those having ordinary skill in the art, that the movements of the rotating drums 142, 144 and the casting belt 140 described above can be readily maneuvered and controlled by motors (not shown) and registration devices (not shown) that are well known and conventional, as discussed hereinabove.

When it is desired to cast a subsequent film segment, with the reciprocating slit extruder 146 now in its second position 196 and the casting belt 140 held stationary, the slidable gate 180 is again moved to a position which opens the slit 170 by an amount that is equal to the thickness desired for the striped film 138. As the stock film forming materials 166, 168 flow out of the chambers 158, 160, 162, 164 and onto the casting belt 140, the reciprocating slit extruder 146 is moved from its second position 196, at a constant predetermined speed, back to its first position 194, where it is again temporarily halted. As the stock film forming materials 166, 168 are being cast onto the casting belt 140, the first edge of the new film segment will meet and bond with the second edge 204 of the first film segment 200. After the reciprocating slit extruder 146 returns to its first position 194, the slidable gate 180 is again moved to its closed position, thereby blocking the slit 170 and temporarily halting the flow of stock film forming materials 166, 168, which results in the creation of a new film segment that is bonded to the first film segment 200.

The foregoing process steps are repeated continuously, resulting in a film casting process that is semi-continuous and which produces a continuous ribbon of transversely striped film 138. The transversely striped film 138 is continuously removed from the casting belt 140 by a scraper or similar, known device (not shown) and advanced in the direction of arrow J in FIG. 17. The transversely striped film 138 is then fed into the rotary die enrobing apparatus 102 for enrobing cores 10 as described above in connection with the first embodiment of the present invention. It is noted that, as shown in FIG. 20, except for the orientation of the recesses 210, 210' on the rotary dies 208, 208' (see FIG. 20) and the orientation of the cores 10 that are dispensed to nip between the rotary dies 208, 208' (see FIG. 20) by the core dispensing means 118, the enrobing apparatus 102 and its method of operation remain substantially unchanged.

Figure 20:
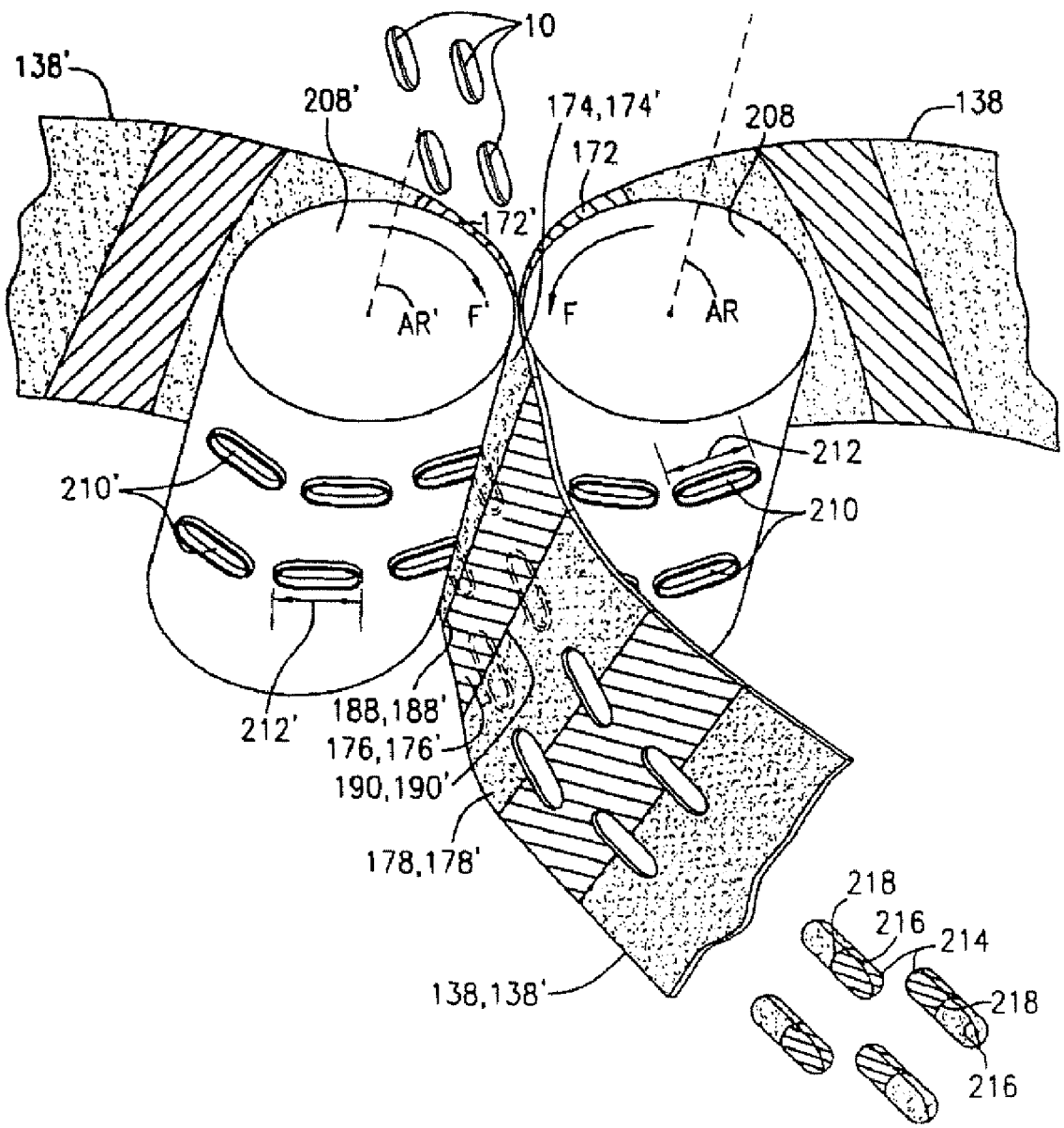
FIG. 20 is a simplified perspective view of the rotating die and striped films, as well as enrobed cores produced thereby, in accordance with the second embodiment of the present invention.
Figure 21:
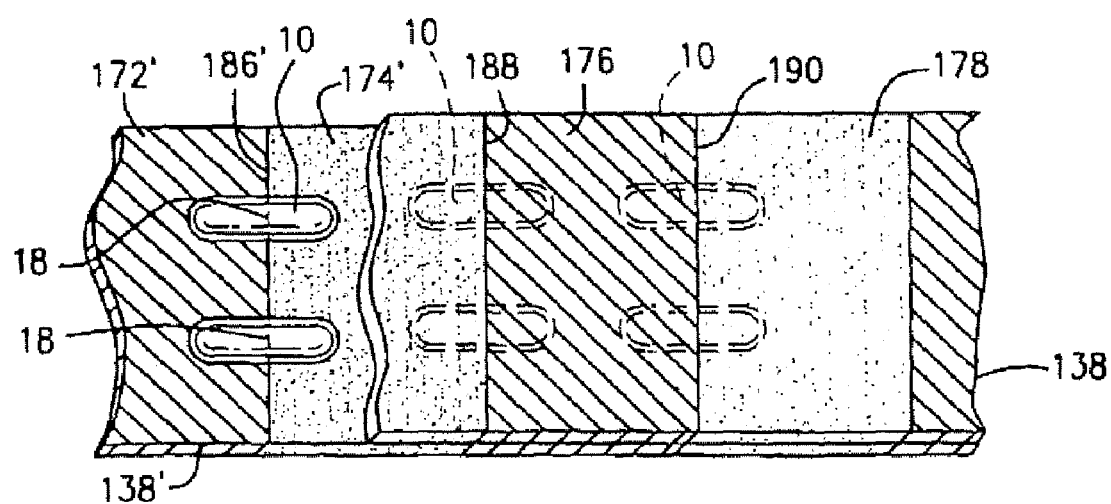
FIG. 21 is a top plan view of a portion of two overlapped striped films with cores placed therebetween, showing the proper orientation of the cores in relation to the stripes on the films.

More particularly, as can be seen in FIG. 20, because the alternative film casting apparatus 136 produces film 138 having stripes 172, 174, 176, 178 that are transversely oriented, the rotary dies 208, 208' of the second embodiment must have recesses 210, 210' which are oriented such that their lengths 212, 212' are aligned perpendicularly to the axes of rotation AR, AR' of their respective rotary dies 208, 208'. In addition, in accordance with the second embodiment, the core dispensing means (not shown) must orient and dispense each core 10 to the nip between the dies 208, 208' end-first, i.e., such that one of the ends 12, 14 of each caplet 10 simultaneously contacts the converging films 138, 138' as the core 10 enters the nip. In such an orientation of the cores 10, the color transitions 186, 188, 190, 186', 188', 190' of the films 138, 138', respectively, lie in the conjugate planes of symmetry 18 of their corresponding cores 10 as the cores 10 enter the nip and are enrobed between the rotary dies 208, 208'. In this regard, FIG. 21 (which is similar to FIG. 15) provides a visual example of the proper positioning of the cores 10, at the nip between the dies 208, 208', in between the transversely striped films 138, 138' and relative to the color transitions 186, 188, 190, 186', 188', 190' thereof, respectively.

As shown in FIG. 20, the resulting gelcap products 214 are bi-colored, having a film seam 216 that lies in the transverse plane of symmetry 16 of the core 10, and having a color transition 218 that lies in the conjugate plane of symmetry 18 of the core 10. The color transition 218 of the gelcap 214 may be flush and seamless, i.e., without any raised portion, and the film coating may be of uniform thickness and color quality over the entire surface of the gelcap 214. If aesthetically desired, the films 138, 138' may be aligned such that the resulting gelcaps 214 have a film seam 216 wherein a stripe of one color or visual distinction (for example, a red stripe 172) of one film 138 abuts or overlaps a stripe of another color or visual distinction (for example, a yellow stripe 178') of the other film 138' to form a gelcap 214 having a "checkerboard pattern" (not shown), i.e., having four quadrants of alternating red and yellow colors or other visual distinctions.

After being cut and released from the bonded films 138, 138' in the same manner as disclosed in U.S. Pat. Nos. 5,146, 730 and 5,459,983, the gelcaps 214 may be collected in collecting chutes and/or conveyors (not shown) and transported to further processing equipment (not shown) for further process steps in which the lubricants may be removed, the gelcaps 214 may be dried and/or, if desired, additional coatings or identifying markings may be added.

As illustrated in FIGS. 22-30, the third embodiment of the present invention is directed to an alternative enrobing apparatus (see, especially, FIGS. 22 and 26), which includes the alternative film casting apparatus 136 of the second embodiment and the transversely striped film 138 produced thereby. In a process described in detail hereinafter, the transversely striped film 138 is fed, along with the cores 10, into the alternative enrobing apparatus to produce bi-colored gelcap products, each having a film seam that only partially circumscribes the gelcap and which lies in a reference plane that is different from the reference plane in which the color transition of the gelcap lies.

With reference initially to FIGS. 22, 23 and 26-30, the alternative enrobing apparatus in accordance with the third embodiment of the present invention includes a conveyor system 220 (see FIG. 22) that comprises a series of horizontally-oriented rollers 222 and pairs of rollers, 224, 226, 228 (see FIGS. 26-30), for supporting and conveying the transversely striped film 138. The conveyor system 220 will be described in greater detail hereinafter in connection with FIG. 26.

It will be recalled that the film 138 has alternate transversely-oriented red stripes 172, 176 and yellow stripes 174, 178 with color transitions 186, 188, 190 therebetween (see, e.g., FIGS. 18 and 20), although, as set forth above, any stock film forming materials having other colors or other visual distinctions or appearances are suitable. A core dispensing means 230 is positioned above the conveyor system 220 and the film 138 for the purpose of dispensing the cores 10 onto the film 138 in the required orientation with respect to the color transitions 186, 188, 190 (see, e.g., FIGS. 25A-25C).

The core dispensing means 230 includes a core hopper 232 for holding the cores 10 to be enrobed prior to their entry into a series of slat feeders 234, 236, which are of a well-known type and are commercially available from DT Lasko Merrill of Leominster, Mass., as well as from Aylward Enterprises, Inc. of New Bern, N.C. and Integrated Packaging Systems, Inc. of Parsippany, N.J. The slat feeders 234, 236 typically include a series of internal brushes and wheels (not shown) that orient the cores as required for proper positioning onto the film 138.

The core dispensing means 230 further includes a core positioning slat 238 and a core plunger 240, which is positioned above the positioning slat 238 and is moved reciprocatingly in the directions shown by the arrow P in FIG. 22 by a conventional motor (not shown), such as a hydraulic motor (not shown), in a well-known manner. A registering means 242 (shown schematically only in FIG. 22) is also included to assist in the proper positioning of the caplets 10 onto the film 138, as described hereinafter. The registering means 242 includes any one of many conventional, known types of optical sensory and control devices (not shown, but discussed above in connection with the first embodiment). The registering means 242 also includes conventional, known mechanical adjusting means (not shown), such as a stepper motor (not shown), for adjusting the speed and position of the advancing film 138 on the conveyor system 220, as necessary. Such stepper motors are commercially available from various sources including, but not limited to, Bayside of Port Washington, N.Y., and are well known to persons having ordinary skill in the art.

The positioning slat 238, more particularly, has a pair of external walls 244, 246, each with a core support rail 248, 250, respectively, one of which is shown in phantom in FIG. 22 and the other of which is partially visible in FIG. 23. The walls 244, 246 are sized and shaped so as to receive therebetween caplets 10 having their transverse planes of symmetry 16 aligned with the length of the walls 244, 246, as can best be seen in FIGS. 25A-25C. The support rails 248, 250 are each attached to the inner surfaces 252, 254, respectively, of the walls 244, 246, and are sized and shaped such that each core 10 within the positioning slat 238 is slideably supported simultaneously by each support rail 248, 250. Moreover, the walls 244, 246 are spaced apart from one another a sufficient distance such that the cores 10 are in frictional, but movable, contact with the inner surfaces 252, 254 of the walls 244, 246. Thus, when the cores 10 are no longer supported by the support rails 248, 250, as described hereinafter, they are temporarily held suspended above the conveyor system 220 and the film 138.

In FIGS. 23 and 24A, it can be seen that the inner corners 256, 258 of the support rails 248, 250 may be rounded to prevent gouging or other physical damage to the cores 10 as they slide therealong. It is noted that, depending upon the configuration of the cores 10, the shape of the inner corners 256, 258 of the support rails 248, 250 can be modified. For example, where the cores 10 have a land 22, the inner corners need not be rounded, but rather, they may be 90-degree corners 256', 258' (as shown in FIG. 24D).

With reference now to FIGS. 24A-24C and 25A-25C, the operation of the core dispensing apparatus 230, and especially the positioning slat 238 and plunger 240, will now be described. It is noted that FIGS. 24A-24C show the positioning slat 238, the plunger 240, the film 138 and cores 10', 10", as viewed from the position of line Q-Q in FIG. 22 and looking in the direction of the arrows. FIGS. 25A-25C show side views of a portion of the positioning slat 238, as well as the plunger 240, the film 138, and cores 10', 10", as seen from within the positioning slat 238 (i.e., as if the nearest wall 244 and corresponding support rail 248 were eliminated).

During continuous operation, which is the preferred mode of operation in accordance with the third embodiment of the present invention, the cores 10 are fed from the hopper 232, through the slat feeders 234, 236, to the positioning slat 238, in a known manner. As they are fed into the positioning slat 238, the cores 10', 10", 10''' are lined up, end 12 to end 14, as shown in FIGS. 25A-25C and 26, and, thereby, each core 10', 10", 10''' is moved along the positioning slat 238 in a substantially continuous manner by the core behind it.

When a core 10' is pushed beyond the support rails 248, 250 and is no longer supported thereby, and when the position of a color transition 186 of the film 138 lies in the conjugate plane of symmetry 18' of the core 10', the registering means 242 signals the motor (not shown), which the moves the plunger 240 in the direction shown by the arrows R, R' in FIGS. 24A and 25A, respectively. The plunger 240 moves in the direction of the arrows R, R' until the core 10' contacts and rests upon the film 138 (see FIGS. 24B and 25B), whereupon the plunger 240 momentarily stops its descent and is then moved in the opposite direction, shown by the arrows S, S' in FIGS. 24B and 25B, respectively. When the plunger 240 reaches its upmost position, as shown in FIGS. 24C, 25C, it momentarily stops, until the next core 10" is moved beyond the support rails 248, 250. The foregoing events are repeated continuously as long as cores 10 are fed and moved through the positioning slat 238.

With reference now, in particular, to FIGS. 26-30, the remaining components of the alternative enrobing apparatus of the third embodiment, as well as their operation, will now be described. More particularly, FIG. 26 shows a schematic perspective view of the positioning slat 238, the conveyor system 220 having specialized rollers 222 and pairs of rollers 224, 226, 228 and a pair of rotary dies 260, 262. It is noted that the rotary dies 260, 262 are similar, but not identical, to the rotary dies 112, 112', 208, 208' of the first and second embodiments discussed earlier hereinabove. As seen in FIG. 26, the rollers 222 and the pairs of rollers 224, 226, 228 of the conveyor system 220 are arranged side-by-side.

More particularly, the beginning portion of the conveyor system 220, i.e., the portion that is located between the alternative film casting apparatus 136 (shown only partially in FIG. 22, see FIG. 17 for full view) and a short distance on the opposite side of the core positioning slat 238 (see FIG. 26), is comprised of horizontally-oriented rollers 222. FIG. 27 shows an elevational end view of a core 10, the film 138 and a horizontally-oriented roller 222, in their relative positions to one another, as seen from the position of line T-T in FIG. 26 and looking in the direction of the arrows.

The film 138 is moved by the horizontally-oriented rollers 222 (see FIG. 22), from the alternative film casting apparatus 136 to a short distance past the positioning slat 238 and plunger 240, by which cores 10 have already been deposited onto the film 138, as described hereinabove. It is noted that the horizontally oriented rollers 222 should be at least as long as the width of the film 138, to ensure sufficient support for the film 138. The horizontally-oriented rollers 222 may spin about their longitudinal axes 264 in the direction shown by the arrow U in FIG. 27.

As shown in FIG. 26, the remaining portion of the conveyor system 220, which is located between a short distance past the positioning slat 238 and the rotary dies 260, 262, is comprised of pairs of rollers 224, 226, 228, rather than the horizontally-oriented rollers 222. As shown schematically in FIG. 26, the individual rollers of sequential pairs of rollers 224, 226, 228 are gradually and sequentially pivoted upward from the horizontal plane, in increments of about 10 degrees for each successive pair of rollers 224, 226, 228, starting proximate to the positioning slat 238, such that, as the film 138 approaches the rotary dies 260, 262, the film 138 is folded longitudinally about the cores 10.

More particularly, the individual rollers 224a, 224b of the pairs of rollers 224 that are located proximately to the positioning slat 238 are pivoted upward a small amount, i.e., about 30 degrees (see FIG. 28 showing the degree to which the individual rollers 224a, 224b at this location are pivoted, as seen approximately from the position of line V-V in FIG. 26 and looking in the direction of the arrows). As shown in FIG. 28, the individual rollers 224a, 224b in these pairs 224 may each spin about their longitudinal axes 266a, 266b in the directions indicated by the arrows Wa, Wb.

By comparison, the individual rollers 226a, 226b of the pairs of rollers 226 that are located further from the positioning slat 238 are pivoted upward by a greater amount, i.e., about 70 degrees (see FIG. 29 showing the degree to which the individual rollers 226a, 226b at this location are pivoted, as seen from the position of line X-X in FIG. 26 and looking in the direction of the arrows). As shown in FIG. 29, the individual rollers 226a, 226b in these pairs 226 each spin about their longitudinal axes 268a, 268b in the directions indicated by the arrows Ya, Yb.

Lastly, as shown in FIGS. 26 and 30, the individual rollers 228a, 228b of the pairs of rollers 228 which are proximate to the rotary dies 260, 262 are configured differently from the other individual rollers 224a, 224b, 226a, 226b. More particularly, the individual rollers 228a, 228b of these pairs of rollers 228 each have a concave central portion 270a, 270b which cooperate to form an opening 272 therebetween that is sized and shaped to allow the film 138 and cores 10 to pass snugly therethrough. Each individual roller 228a, 228b also has a cylindrical upper portion 274a, 274b which cooperate with one another to press the longitudinal edges 276, 278 of the film 138 against one another (see FIG. 30), thereby bonding the longitudinal edges 276, 278 of the film 138 to one another prior to passing through the rotary dies 260, 262. FIG. 30 shows that the individual rollers 228a, 228b of the pairs of rollers 228 at this location are oriented substantially vertically, as seen from the position of line Z-Z in FIG. 26 and looking in the direction of the arrows. As also shown in FIG. 30, the individual rollers 228a, 228b of these pairs of rollers 228 may each rotate about their longitudinal axes 280a, 280b in the directions indicated by the arrows AAa, AAb.

It is noted that different configurations are possible for the individual rollers 224a, 224b, 226a, 226b, 228a, 228b and the pairs of rollers 224, 226, 228, for example, one roller 224a, 226a, 228a in each pair could be horizontally positioned and remain stationary, while the other roller 224b, 226b, 228b in each pair is pivoted. In addition, depending upon the support requirements of the film 138, greater or fewer numbers of horizontally-oriented rollers 222 and pairs of rollers 224, 226, 228 may be used for the conveyor system 220 and they may be spaced more closely or further apart than shown in the accompanying figures.

The rotary dies 260, 262 of the third embodiment of the present invention, shown in FIG. 26, are similar to the rotary dies 112, 112', 208, 208' of the first and second embodiments in that they rotate in the directions indicated by the arrows BB and CC, respectively, in FIG. 26, thereby cooperating with one another to form a nip therebetween, into which the cores 10 and the film 138 are fed. Likewise, each of the dies 260, 262 have recesses 282, 284, arranged circumferentially in a row on the surface of each die 260, 262. The recesses 282, 284 each have raised rims (not shown) for sealing and cutting the bonded film 138 about the cores 10, thereby enrobing the cores 10 to form gelcap products 286.

The rotary dies 260, 262 of the third embodiment, however, are oriented such that they rotate in the horizontal plane, rather than in the vertical plane as do the previously discussed rotary dies 112, 112', 208, 208'. Furthermore, when the cores 10 are fed into the nip between the dies 260, 262 of the third embodiment, the film 138 is folded and partially bonded about them. Furthermore, the partially enrobed caplets 10 are fed successively, i.e., one-by-one, into the nip between the dies 260, 262.

The gelcap products 286 of the third embodiment are similar to the gelcaps 122, 214 of the previous embodiments, in that they are gelcaps 286 having at least two visually distinct, or differently colored, portions and having film seams 288 which are transversely oriented relative to the color transitions 290 (or other visual distinction transitions) of the gelcaps 286. More particularly, the film seam 288 lies in the transverse plane of symmetry 16 of the core 10 and the color transition 290 lies in the conjugate plane of symmetry 18 of the core 10. In addition, in contrast to gelcaps produced by apparatus and methods of the prior art, the color transition 290 of the gelcap 286 of the third embodiment may be flush and seamless, i.e., without any raised portion which generally characterizes the film seam 288 of gelcaps. Moreover, the gelcaps 286 may have a film coating of uniform color quality and thickness over their entire surface. It is noted, however, that unlike the gelcaps 122, 214 of the previously described embodiments, the film seams 288 of the gelcaps 286 that are produced by the apparatus and process of the third embodiment extend only partially about the cores 10. If aesthetically desired, the film 138 may overlap slightly at its edges along the film seam 288.

As will be appreciated by those persons with ordinary skill and experience in the present field, it is possible to substitute other known, conventional cutting devices in place of the rotary dies 260, 262 shown in FIG. 26. For example, die punches (not shown), or reciprocating uniplasts (not shown), having recesses or cutouts that are sized and shaped to receive therein the partially enrobed caplets 10 could be used. Such devices are commercially available from various sources, including, but not limited to, The Irwin-Hodson Company of Portland Oreg., and are well-known to those having ordinary skill in the art. In addition, alternative reciprocating cutting apparatus which relates to producing enrobed capsule products is disclosed in U.S. Pat. No. 6,352,719, which is hereby incorporated by reference herein.

With reference to the movement of the transversely striped film 138 along the conveyor system 220 of horizontally-oriented rollers 222 and pairs of rollers 224, 226, 228, it is noted that the film 138 is encouraged to move, continuously and at a substantially constant speed, in the direction of the arrow DD in FIG. 26, by the nip between the rotary dies 260, 262 and the momentum of the horizontally-oriented rollers 222 and the pairs of rollers 224, 226, 228 as they spin about their axes. Alternatively, or in addition thereto, one or more of the horizontally-oriented rollers 222 and the pairs of rollers 224, 226, 228 could be mechanized by conventional motors (not shown) to spin autonomously, thereby encouraging the film 138 to move along the conveyor system 220 toward the rotary dies 260, 262.

With reference to the stock film forming material that is used in connection with the foregoing alternative core enrobing apparatus of the third embodiment, when it is either thermoplastic starch-based material or cellulose-based material, as suggested hereinabove, the transversely striped film 138 must be heated prior to being advanced along the portion of the conveyor system 220 that is comprised of pivoted pairs of rollers 224, 226, 228 to ensure that the film 138 is sufficiently formable and malleable to be folded about the caplets 10 by the pairs of rollers 224, 226, 228, while maintaining its physical integrity. In such circumstances, the film 138 can be heated by conventional heating means, such as, for example, a resistive heating device (not shown) which would heat the film 138 indirectly by heating selected horizontally-oriented rollers 222 and pairs of rollers 224, 226, 228, or hot air blowers (not shown) which could heat the film 138 directly by blowing hot air thereon. Suitable heaters are commercially available, for example, from Chromolox, Inc. of Pittsburgh, Pa. and Watlow Electric Manufacturing Company of St. Louis, Mo. Suitable hot air blowers are commercially available, for example, from New York Blower Company of Willowbrook, Ill. and Niagara Blower Company of Buffalo, N.Y.

More particularly, where the film 138 is made of starch-based material, the film 138 should be heated to between about 50 degrees Celsius and about 150 degrees Celsius and where the film 138 is made of cellulose-based material, the film 138 should be heated to between about 80 degrees Celsius and about 120 degrees Celsius.

The fourth embodiment of the present invention, which relates to a vacuum forming apparatus and method of enrobing cores is generally illustrated in FIGS. 31-43. It is noted that, while various types of thermal formable films, including films made of the previously discussed gelatin-, starch- and polymer-based materials, may be used in connection with the fourth embodiment of the present invention, films made of cellulose ether-based materials, e.g. hydroxypropyl methylcellulose, are the preferred films to be used in connection with the apparatus and method described hereinafter. However, while the composition of the film may be the same or similar to that of the films discussed hereinabove, the film that is used in connection with the apparatus of the fourth embodiment is pre-manufactured as a dry film, rather than the wet films that were described previously in connection with the first, second and third embodiments.

More particularly, to produce films that are suitable for use with the vacuum forming apparatus of the fourth embodiment, the wet films of the previous embodiments are subjected to a further drying step, which involves heating the film, in a manner that is well-known to the art of film forming, to a temperature such that the film remains pliable, but no longer automatically bonds to itself upon contact. The dried film is then mounted onto rollers, as shown and described hereinafter in connection with FIG. 31. In addition, the dry films used in this fourth embodiment may also be subjected to further processing steps, including, but not limited to, the addition of humectants or plasticizers, such as glycerin or sorbitol, for the purpose of enhancing the elasticity and formability of the dry films. For example, from 0.1 to 10 weight percent of humectants, based upon the total weight of the dry film material, could be added to the dry films. In addition, from 5 to 50 weight percent of plasticizers, based upon the total weight of the dry film material, could be added to the dry films. It is also noted that, as discussed hereinafter, striped films having stripes that are either longitudinally or transversely oriented may be used in connection with the apparatus and method of the fourth embodiment, which will now be described in detail. Films having a thickness of between about 0.01 millimeters and about 0.5 millimeters are most suitable for use in connection with this fourth embodiment of the present invention.

Figure 31:
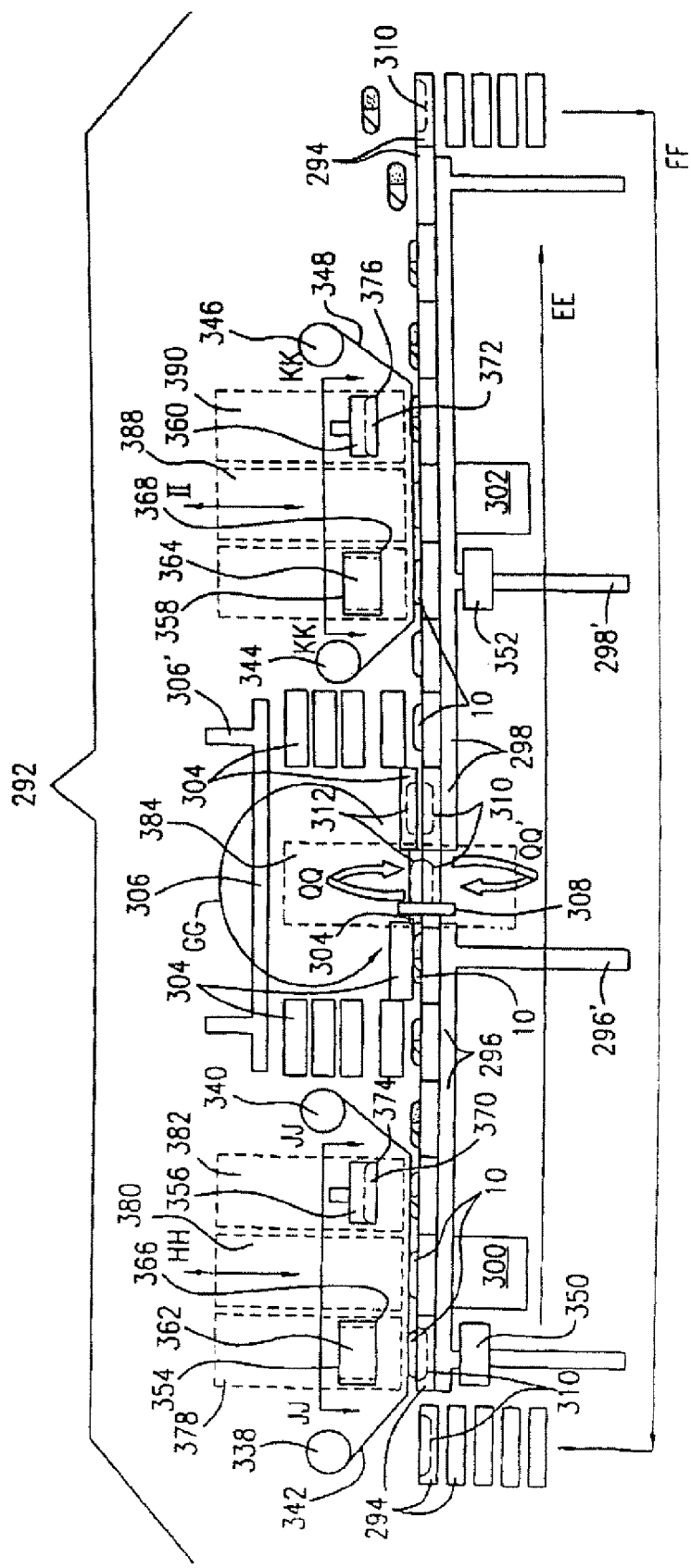
FIG. 31 is a schematic elevational side view of the apparatus of the fourth embodiment.

With reference, in particular, to FIG. 31, a schematic elevational side view is provided of the vacuum forming apparatus 292 of the fourth embodiment. More particularly, the vacuum forming apparatus 292 includes a first plurality of individual porous platens 294, as well as a first conveyor system 296 and a second conveyor system 298. As shown schematically in FIG. 31, the first and second conveyor systems 296, 298 are arranged in series with one another, thereby creating a single path, indicated by the arrows EE, FF, along which the first and second conveyor systems 296, 298 move each of the porous platens 294 in semi-continuous fashion. For purposes of illustration only, the first and second conveyor systems 296, 298 are shown schematically in FIG. 31 mounted on tables 296', 298'. In addition, the first and second conveyer systems 296, 298 are provided with conventional vacuum sources 300, 302, respectively, (shown only schematically in FIG. 31) that apply a vacuum to each of the porous platens 294 while they are moved in the direction shown by the arrow EE, for a purpose to be discussed hereinafter. Suitable conventional vacuum sources, such as vacuum pumps, would be commercially available from, for example, The Nash Company of Trumbull, Conn. and Gast Manufacturing of Benton Harbor, Mich.

It is noted that the first and second conveyor systems 296, 298 each include a conveyor mechanism, such as a conventional chain track (not shown) or other conventional mechanism of a type that is known in the art. More particularly, conveyor systems suitable for use in connection with the vacuum forming apparatus 292 of the present invention are typically custom manufactured and persons having ordinary skill in the art will be familiar with the basic configuration and operation of such devices. Suitable conveyor systems are currently commercially available from, for example, Dorner of Hartland, Wis.

With reference still to FIG. 31, the vacuum forming apparatus 292 further includes a second plurality of individual porous platens 304 and a third conveyor system 306 that moves these porous platens 304 along a second path, which is shown by the arrow GG in FIG. 31. It is noted that the third conveyor system 306 is positioned between the first and second conveyor systems 296, 298 for a purpose that is clarified hereinafter.

A rotating mechanism 308 (shown only schematically in FIG. 31) is positioned between the first and second conveyor systems 296, 298. The rotating mechanism 308 is a conventional device and well known to persons having ordinary skill in the art. The rotating mechanism 308 is designed to simultaneously hold together two of the platens, i.e., one platen 294 and a corresponding platen 304, and rotate them together, such that the platen 304 that is first on top is inverted and then positioned on the bottom after the rotation is completed. The aforesaid rotation will be described in further detail hereinafter.

Figure 35:
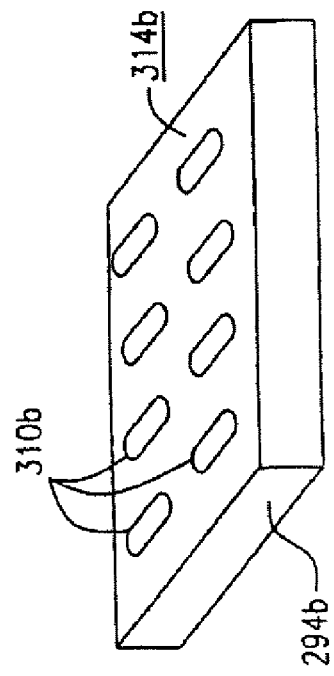
FIG. 35 is a schematic perspective view of a porous platen having a plurality of recesses arranged in rows and suitable for use with the longitudinally-striped film of FIG. 34.
Figure 33:
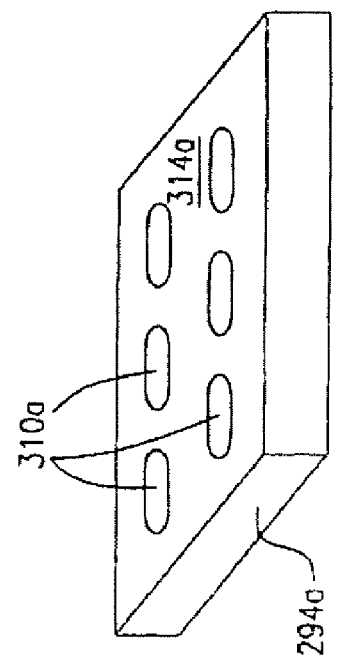
FIG. 33 is a schematic perspective view of a porous platen having a plurality of recesses arranged in rows and suitable for use with the transversely-striped film of FIG. 32.

Except for their opposite orientations, the porous platens 294, 304 are essentially identical to one another. More particularly, as shown in phantom in certain of the porous platens 294, 304 in FIG. 31, each porous platen 294, 304 has at least one recess 310, 312, respectively, on a working surface 314, 316, respectively, thereof. Each recess 310, 312 is sized and shaped to temporarily but snugly receive therein a caplet 10 to be enrobed. With reference to FIGS. 33 and 35, it is noted that, although the porous platens 294, 304 are shown in FIG. 31 as each having a single longitudinally oriented recess 310, 312, it is noted that the porous platens 294, 304 may be configured to each have a plurality of recesses 310, 312. For example, the platens 294, 304 could each be long enough to include a single row of recesses 310, 312, or, as shown in FIGS. 33 and 35, each platen 294a, 294b could be long and wide enough to have multiple rows of recesses 310a, 310b.

Figure 32:
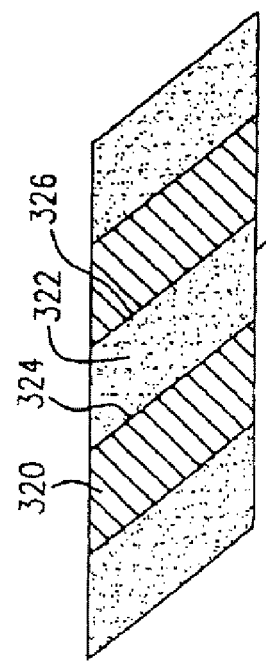
FIG. 32 is a schematic perspective view of a tranversely-striped film suitable for use with a porous platen having a plurality of recesses arranged in rows.

In addition, it is noted that, if the orientation of the recesses 310a, 310b of the platens 294a, 294b is varied, the use of differently striped films can be accommodated, as follows. With reference to FIGS. 32 and 33, where the recesses 310a are oriented longitudinally on the working surface 314a of the porous platen 294a (see FIG. 33) it is possible to use a striped film 318 having alternating colors or visual distinctions, e.g., red and yellow transverse stripes 320, 322 (see FIG. 32), to produce gelcap products having a color transition (or other visual distinction transition) that lies in the conjugate plane of symmetry 18 of the core 10. The resulting product would resemble gelpcaps 122, 214, 286 produced in connection with the previously discussed embodiments of the present invention. In FIGS. 32 and 33, the transversely striped film 318 is shown suspended above the platen 294*a* in the proper position relative to the recesses 310*a*, such that the color transitions 324, 326 between the transverse stripes 320, 322 are properly aligned with the recesses 310*a* to result in the production of the aforesaid bi-colored enrobed core products.

Figure 34:
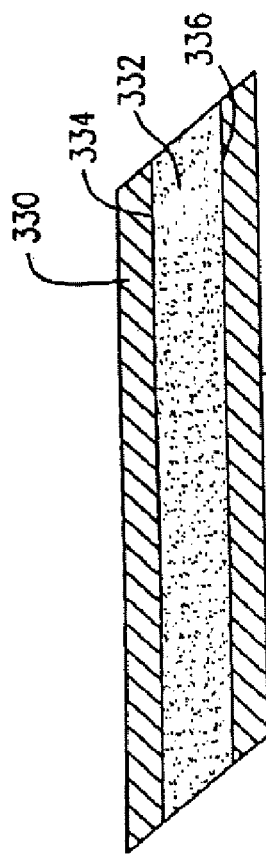
FIG. 34 is a schematic perspective view of a longitudinally-striped film suitable for use with a porous platen having a plurality of recesses arranged in rows.

With reference to FIGS. 34 and 35, on the other hand, it is possible for the recesses 310*b* to be oriented transversely on the working surface 314*b* of the porous platen 294*b* (see FIG. 35) to accommodate the use of a striped film 328 having alternating colors or visual distinctions, e.g., red and yellow longitudinal stripes 330, 332 (shown in FIG. 34), to produce gelcap products having a color transition lying in the conjugate plane of symmetry 18 of the core 10. In FIGS. 34 and 35, the longitudinally striped film 328 is shown suspended above the platen 294*b* in the proper position relative to the recesses 310*b*, such that the color transitions 334, 336 between the longitudinal stripes 330, 332 are properly aligned with the recesses 310*b* to result in the production of the aforesaid bi-colored caplet products.

It is of course possible to achieve multi-colored gelcap products having color transitions oriented in a variety of different ways using different combinations of the platens 294*a*, 294*b* shown in FIGS. 33 and 35, with transversely and longitudinally striped films 318, 328, shown in FIGS. 32 and 34. In this regard, however, it is noted that, within a particular vacuum forming apparatus, the orientation of the recesses 310, 312 in all of the platens 294, 304 must be longitudinal, or, alternatively, the orientation of the recesses 310, 312 in all of the platens 294, 304 must be transverse (or otherwise aligned with the orientation of the stripes on the films).

With reference again to FIG. 31, the vacuum forming apparatus 292 further includes a first pair of rollers 338, 340 having a first striped film 342 mounted thereon. As shown in FIG. 31, the first pair of rollers 338, 340 is positioned proximate to the first conveyor system 296 such that the first striped film 342 is suspended above the first plurality of porous platens 294, which are being moved thereon along the path shown by the arrow EE. A second pair of rollers 344, 346 having a second striped film 348 mounted thereon is also provided. Like the first pair of rollers 338, 340, the second pair of rollers 344, 346 is positioned proximate to the second conveyor system 298 such that the second striped film 348 is also suspended above the first plurality of porous platens 294, which are being moved thereon along the path shown by the arrow EE.

It is noted that, in order to produce gelcaps having a color transition, or transition between other visually distinct portions of the enrobed core 10, that lies in the conjugate plane of symmetry 18 of the core 10 using platens 294*a* like those of FIG. 33 (i.e., all having longitudinally oriented recesses 310*a*), both the first and second striped films 342, 348 must have transversely oriented stripes 320, 322, as shown in FIG. 32. Similarly, in order to produce bi-colored gelcaps still having a color transition that lies in the conjugate plane of symmetry 18 of the caplet 10 using platens 294*b* like those of FIG. 35 (i.e., all having transversely oriented recesses 310*b*), it would be necessary for both the first and second striped films 342, 348 to have longitudinally oriented stripes, as shown in FIG. 34.

The above-described variations concerning the orientation of the recesses 310, 312 on the platens 294, 304 and the orientation of the stripes on the first and second films 342, 348 are all equally valid. However, for purposes of illustrating the fourth embodiment of the present invention in as simple and clear a manner as possible, henceforth, it will be understood that the platens 294, 304 of the vacuum forming apparatus 292 each have a single longitudinally oriented recess 310, 312 thereon. Furthermore, it will henceforth also be understood that the first and second striped films 342, 348 both have alternating red and yellow stripes that are transversely oriented.

As shown in FIG. 31 and discussed in further detail hereinafter, the vacuum forming apparatus 292 also includes a first registering device 350 positioned proximate to the first conveyor system 296 for properly positioning the first transversely striped film 342 relative to a core 10 that is positioned within the recess 310 of the porous platen 294, as will be described hereinafter. A second registering device 352 is positioned proximate to the second conveyor system 298 for properly positioning the second transversely striped film 348 relative to a partially enrobed caplet 10 that is positioned within the recess 310 of another of the porous platens 294, as will be described hereinafter. The registering devices 350, 352 are of the same commercially available type as were described previously above in connection with the first embodiment of the present invention.

As shown in FIGS. 31, 36-38 and 41-43, the vacuum forming apparatus 292 of the fourth embodiment also includes a first ring press 354 and a first film cutter 356 that are positioned proximate to the first conveyor system 296, for purposes that will be clarified hereinafter. Additionally, a second ring press 358 and a second film cutter 360 are positioned proximate to the second conveyor system 298, also for purposes that will be clarified hereinafter. More particularly, with reference to FIGS. 36-37 and 41-42, the first and second ring presses 354, 358 are virtually identical to one another, each having an open configuration, such as an O-shape or an oval shape, as viewed from above, such that there is formed a passageway 362, 364, respectively, therethrough. Each of the ring presses 354, 358 also has a contacting edge 366, 368, respectively, that is configured to contact the first and second films 342, 348, respectively, without damaging them. Each of the ring presses 354, 358 is sized and shaped such that the contacting edges 366, 368 circumscribe a core 10 therein. The first and second ring presses 354, 358 move reciprocatingly in the directions shown by the arrows HH, II, respectively, in FIG. 31.

Figures 38, 39:
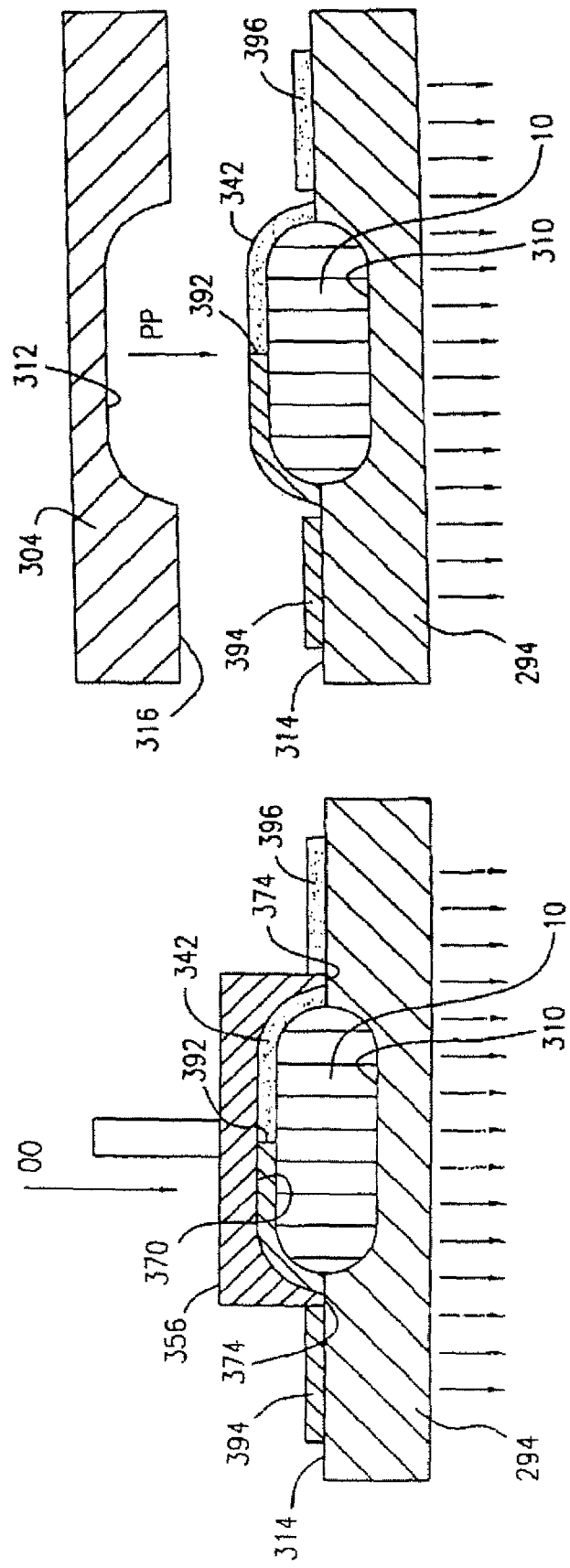
FIG. 38 is a partial, schematic, cross-sectional elevational side view of a third station of the apparatus of the fourth embodiment, with the near cross-sectional half cut away therefrom, showing how the film is cut away from the perimeter of the partially enrobed core.
FIG. 39 is a partial, schematic, cross-sectional elevational side view of a fourth station of the apparatus of the fourth embodiment, with the near cross-sectional half cut away therefrom, showing how the partially enrobed core thereon is positioned beneath an inverted porous platen for transfer thereto.

With reference, in particular, to FIGS. 38 and 43, the first and second film cutters 356, 360 are virtually identical to one another, each having a recess 370, 372, respectively, that is sized and shaped to receive therein a portion of a partially enrobed core 10 which already has a film coating applied thereto. Each recess 370, 372 is circumscribed by a tapered cutting edge 374, 376 that is sized and shaped to closely circumscribe the periphery of the aforesaid partially enrobed core 10 and is capable of cutting neatly and cleanly through the first and second transversely striped films 342, 348, respectively. The first film cutter 356 is oriented such that its recess 370 and cutting edge 374 both face the porous platen 294 positioned thereunder. Similarly, the second film cutter 360 is oriented such that its recess 372 and cutting edge 376 also both face the porous platen 304 positioned thereunder. Also, like the ring presses 354, 358, the first and second film cutters 356, 360 move reciprocatingly in the directions shown by the arrows HH, II in FIG. 31.

With reference still to FIG. 31, it is noted that the first transversely striped film 342 is mounted onto a first pair of rollers 338, 340 and stretched therebetween, such that the first film 342 is positioned between the first conveyor system 296 and the first plurality of porous platens 294 on one side, and the first ring press 354 and the first film cutter 356 on the other side. Similarly, the second transversely striped film 348 is mounted onto a second pair of rollers 344, 346 and stretched therebetween, such that the second film 348 is positioned between the second conveyor system 298 and the first plurality porous platens 294 on one side, and the second ring press 360 and the second film cutter 362 on the other side.

As will be referred to subsequently herein, in connection with the description of the method of the fourth embodiment, the vacuum forming apparatus 292 shown in FIG. 31 includes at least seven stations 378, 380, 382, 384, 386, 388, 390 (shown in dotted lines in FIG. 31), each of which is shown in further detail in FIGS. 36-43. The aforesaid stations 378, 380, 382, 384, 386, 388, 390 show the general locations of the ring presses 354, 358, and the film cutters 356, 360, relative to the other components of the vacuum forming apparatus 292. The stations 378, 380, 382, 384, 386, 388, 390 also provide a conceptual representation of the seven basic steps of the method of the fourth embodiment.

The operation of the vacuum forming apparatus 292 and the method of the fourth embodiment of the present invention will now be described in detail, with reference to FIGS. 31 and 36-44. In this regard, it is noted that FIGS. 36-44 show elevational cross-sectional views of certain components of the vacuum forming apparatus 292. More particularly, the cross-sections of the platens 294, the first ring press 354 and the first film cutter 356 shown in FIGS. 36-39 are taken along cross-section line JJ-JJ of FIG. 31 and are viewed from the same direction as when viewing the vacuum forming apparatus 292 shown in FIG. 31. The cross-sections of the platens 304, the second ring press 358 and the second film cutter 360 shown in FIGS. 40-43 are taken along cross-section line KK-KK of FIG. 31 and are also viewed from the same direction as when viewing the vacuum forming apparatus 292 shown in FIG. 31. It is further noted that the conveyor systems 296, 298, the registering devices 350, 352 and the vacuum sources 300, 302 are omitted from FIGS. 36-43 to simplify the description of the operation of the vacuum forming apparatus 292, by which cores 10 are enrobed with the first and second transversely striped films 342, 348.

Initially, the first, second and third conveyor systems 296, 298, 306 are set into motion, thereby moving the porous platens 294, 304 in the directions indicated by the arrows EE, FF, GG, respectively, in FIG. 31. The vacuum sources 300, 302 are also activated, thereby applying vacuums, in the range of about 0.005 Torr to about 700 Torr, to the first and second conveyor systems 296, 298, and, thereby in turn, to each of the first plurality of porous platens 294 that is being moved in the direction of the arrow EE.

More specifically, with reference initially to FIG. 31, the first conveyor system 296 moves one of the porous platens 294 to a position that is immediately prior to the first station 378. A core 10 is placed into the recess 310 of this porous platen 294 by a core dispensing mechanism (not shown). It is noted that the core dispensing mechanism of this fourth embodiment can be any one of conventional, well-known core dispensing mechanisms, such as those described previously in connection with the first, second and third embodiments. The core 10 is held firmly in the recess 310 by the aforementioned vacuum, which is continuously applied to the platen 294 and all others on the conveyor 298, by the first vacuum source 300.

Figure 36:
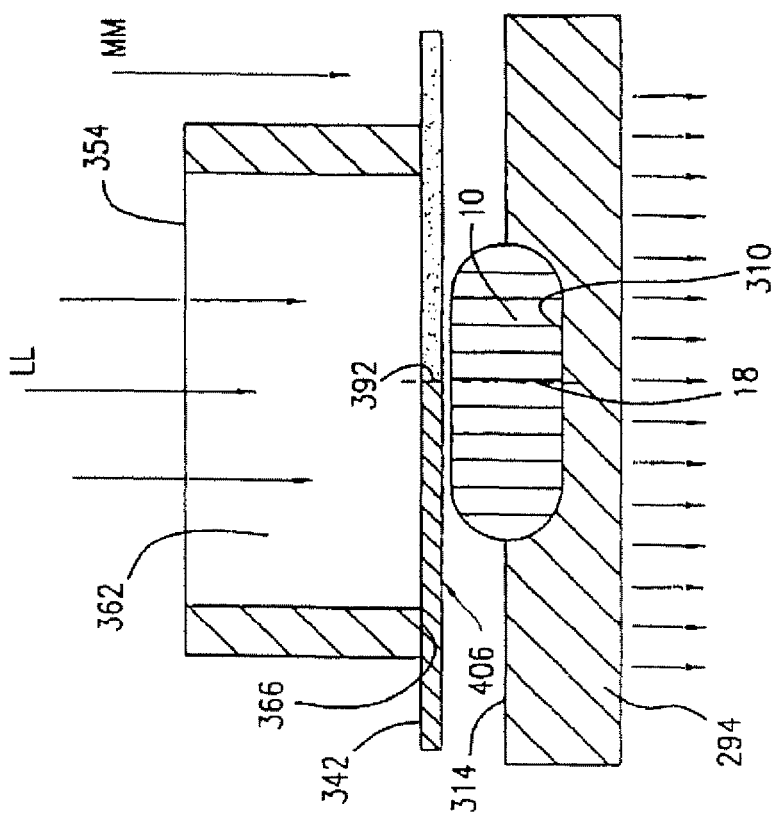
FIG. 36 is a partial, schematic, cross-sectional elevational side view of a first station of the apparatus of the fourth embodiment, with the near cross-sectional half cut away therefrom, showing how the film is heated and vacuum formed about one half of the core.

With reference now to both of FIGS. 31 and 36, the platen 294 is next moved by the first conveyor system 296 to the first station 378. Movement of the platen 294 ceases temporarily when the first registering device 350 (see FIG. 31) confirms that the core 10 is properly positioned relative to the first striped film 342, i.e., such that the color transition 392 of the first striped film 342 (see FIG. 36) lies in the conjugate plane of symmetry 18 of the core 10.

While the platen 294 is momentarily stationary, hot air is blown, by conventional, well-known means, such as a combined coil heater and fan device (not shown), through the passageway 362 of the first ring press 354, in the direction shown by the arrows LL in FIG. 36, thereby softening the first film 342 to a formable state. The hot air should, preferably, be in the range of between about 50 degrees Celsius and about 300 degrees Celsius, depending upon the type of film used. The first ring press 354 is then moved in the direction shown by the arrow MM in FIG. 36, such that the contacting edge 366 of the first ring press 354 presses the first film 342 onto the working surface 314 of the platen 294 and into contact with the top half of the core 10.

Figure 37:
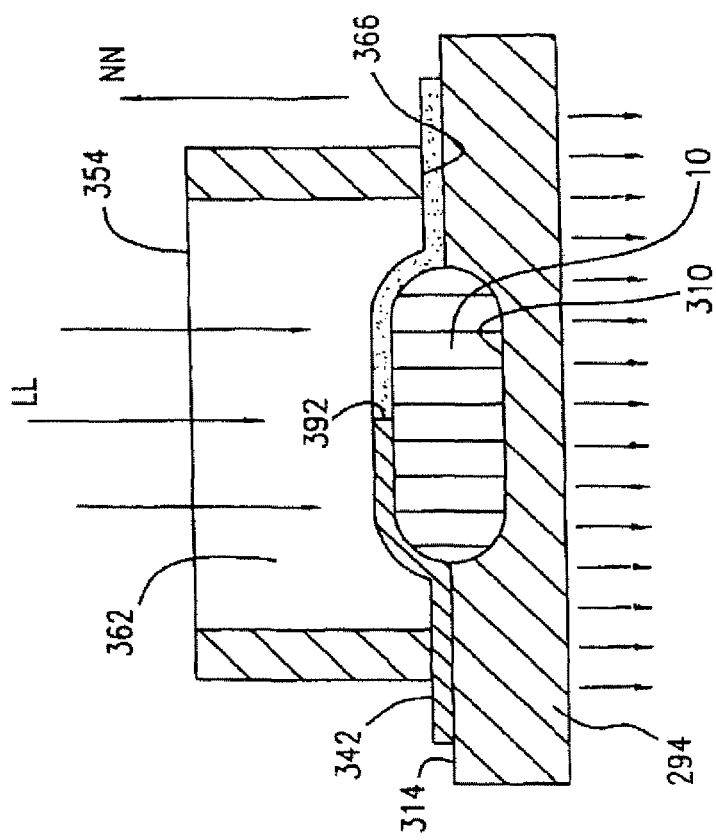
FIG. 37 is a partial, schematic, cross-sectional elevational side view of a second station of the apparatus of the fourth embodiment, with the near cross-sectional half cut away therefrom, showing how the film is cooled and molded about one half of the core.

As shown in FIG. 37, the heated first film 342 is simultaneously pulled onto the core 10 and thereby made to conform to the shape of the top half of the core 10 by the aforementioned vacuum that is applied to the platen 294 by the first vacuum source 300. The vacuum applied by the first vacuum source is in the aforesaid range of about 0.005 Torr to about 700 Torr. Thereafter, the first ring press 354 is moved away from the platen 294, in the direction shown by the arrow NN in FIG. 37, while the heated first film 342 is held onto the core 10 by the aforesaid vacuum.

With continued reference to FIG. 37, after the first ring press 354 is retracted, the platen 294, having the partially enrobed core 10 held in its recess 310 by the vacuum, is moved to the second station 380 of the vacuum forming apparatus 292, where it is temporarily stopped. While the platen 294 and the core 10 are temporarily stationary, cold air is blown onto the first film 342 and core 10 in the direction shown by the arrows LL in FIG. 37, thereby cooling and molding the first film 342 into conformity with the top half of the core 10. The cold air should be at a temperature that is sufficiently cool to stiffen the film 342 such that it retains its shape in conformity with the shape of the core 10, more particularly between about −10 degrees Celsius and about 25 degrees Celsius.

With reference now to FIG. 38, after sufficient time has passed to cool and mold the first film 342 onto the core 10, the platen 294 and partially enrobed core 10 are moved a predetermined distance by the first conveyor system 296 to the third station 382 of the vacuum forming apparatus 292 and temporarily halted there such that the partially enrobed core 10 is aligned with the recess 370 and the cutting edge 374 of the first film cutter 356. As shown in FIG. 38, the first film cutter 356 is moved in the direction of the arrow OO until the partially enrobed core 10 is received snugly within the recess 370 and the tapered cutting edge 374 contacts and cuts through the first film 342 closely around the perimeter of the partially enrobed core 10. The first film cutter 356 is then moved away from the platen 294 in a direction opposite the direction indicated by the arrow OO and scrap portions 394, 396 of the first film 342 are removed from the platen 294.

Figure 40:
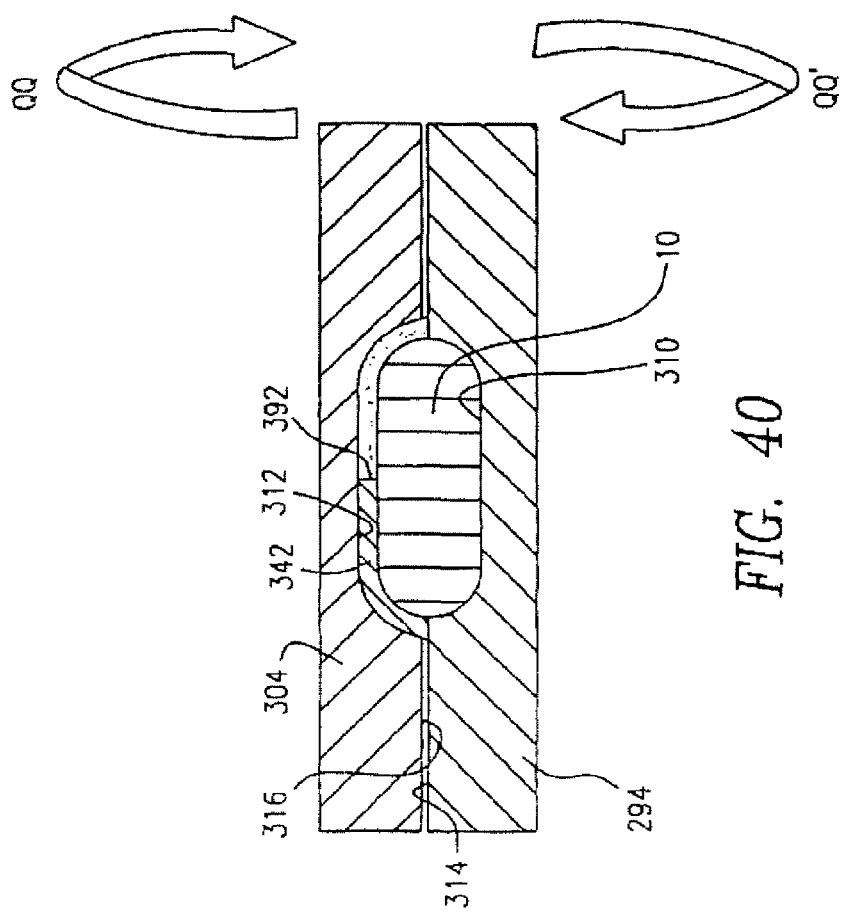
FIG. 40 is a partial, schematic, cross-sectional elevational side view of the fourth station of FIG. 39, showing how the inverted porous platen is lowered onto the partially enrobed core and how the two platens and partially enrobed core are subsequently rotated together.

With reference now to FIGS. 39 and 40, the platen 294 and partially enrobed core 10 are next moved to the fourth, or rotating, station 384 of the vacuum forming apparatus 292 and, again, temporarily stopped, whereupon the partially enrobed core 10 is transferred to one of the platens 304, as follows. As shown in FIG. 39, the third conveyor system 306 moves one of the platens 304 into position at the rotating station 384, such that it 304 is inverted relative to the platen 294 carrying the partially enrobed core 10 thereon. It is noted that the working surfaces 314, 316 of the platens 294, 304 are facing one another (see FIGS. 31, 39 and 40). After the platen 294 is moved a predetermined distance, such that the partially enrobed core 10 is aligned with the recess 312 of the inverted platen 304, the first conveyor system 296 holds the platen 294 and partially enrobed core 10 temporarily stationary at the rotating station 384. The platen 304 is then moved toward the partially enrobed core 10 (i.e., in the direction shown by the arrow PP in FIG. 39) until the partially enrobed core 10 is held within the recesses 310, 312 of both of the platens 294, 304 (as shown in FIGS. 31 and 40). The vacuum being applied to the porous platen 294 is discontinued and the rotating mechanism 308 (shown schematically in FIG. 31) rotates the platens 294, 304, with the partially enrobed core 10 therebetween, in the direction shown by the arrows QQ, QQ' in FIGS. 31 and 40, whereupon the platen 294 holding the core 10 is inverted, and the platen 304 is moved into a right-side-up position. The now inverted platen 294 is now moved away from the right-side-up platen 304 and becomes one of the platens 304 moving along the path shown by the arrow GG in FIG. 31. The right-side-up platen 304 is next moved onto the second conveyor system 298 and becomes one of the platens 294 moving along the path shown by the arrows EE, FF in FIG. 31. Next, the second vacuum source 302 applies a vacuum, in the aforesaid range of about 0.005 Torr to about 700 Torr, to the partially enrobed core 10, thereby holding the partially enrobed core 10 within the recess 310 of the platen 294, which is now moving on the second conveyor system 298, such that the uncovered portion of the partially enrobed core 10 is exposed.

Figure 41:
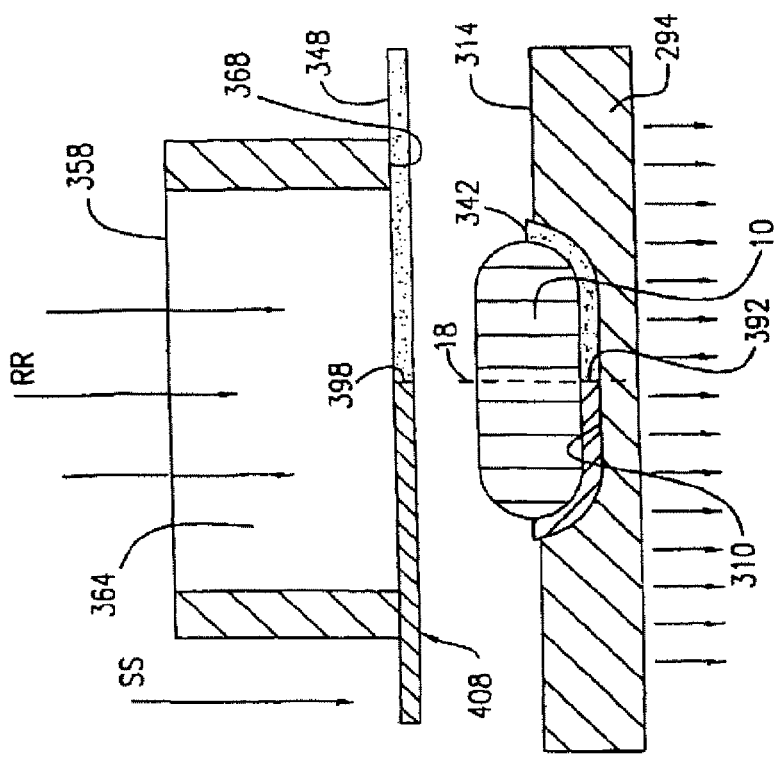
FIG. 41 is a partial, schematic, cross-sectional elevational side view of a fifth station of the apparatus of the fourth embodiment, with the near cross-sectional half cut away therefrom, showing how a second film is heated and vacuum formed about the uncovered portion of the core.

FIGS. 41-43 show, schematically, the method by which the uncovered portion of the core 10 is covered by the second transversely striped film 248. More particularly, with reference in particular to FIG. 41, the platen 294 and partially enrobed core 10 are moved by the second conveyor system 298 to the fifth station 386 of the vacuum forming apparatus 292. Movement of the platen 294 ceases temporarily when the second registering device 352 (see FIG. 31) confirms that the partially enrobed core 10 is properly positioned relative to the second striped film 248, i.e., such that the color transition 398 of the second striped film 348 (see FIG. 41) lies in the conjugate plane of symmetry 18 of the partially enrobed core 10.

While the platen 294 is momentarily stationary, hot air is blown, by conventional, well-known means, such as a combined coil heater and fan device (not shown), through the passageway 364 of the second ring press 358, in the direction shown by the arrows RR in FIG. 41, which softens the second film 348 to a formable state. The hot air is preferably in the aforesaid range of about 50 degrees Celsius to about 300 degrees Celsius. The second ring press 358 is then moved in the direction shown by the arrow SS in FIG. 41, such that the contacting edge 368 of the second ring press 358 contacts and presses the second film 348 onto the working surface 314 of the platen 294 and into contact with the uncovered portion of the partially enrobed core 10.

As shown in FIG. 42, the heated second film 248 is then pulled onto the core 10 by the vacuum that is applied by the second vacuum source 302 (see FIG. 31), in the aforesaid range of about 0.005 Torr to about 700 Torr, to the platen 294, thereby conforming the second film 248 to the shape of the uncovered portion of the core 10. Thereafter, the second ring press 358 is moved away from the platen 294, in the direction shown by the arrow TT in FIG. 42, while the heated second film 248 is held onto the core by the aforesaid vacuum applied by the second vacuum source 302.

With continued reference to FIG. 42, after the second ring press 358 is retracted, the platen 294, having the enrobed core 10 held in its recess 310 by the vacuum, is now moved to the sixth station 388 of the vacuum forming apparatus 292 and temporarily stopped there. It is noted that, as shown in FIG. 42, the second film 348 partially overlaps the cut edge of the first film 342 that has already been applied to the core 10. While the platen 294 and the core 10 are temporarily stationary, cold air, in the aforesaid range of about −10 degrees Celsius to about 25 degrees Celsius, is now blown onto the second film 248 and core 10 in the direction shown by the arrows RR in FIG. 42, thereby cooling and molding the second film 348 into conformity with the core 10.

With reference now to FIG. 43, after sufficient time has passed to cool and mold the second film 348 onto the core 10, the platen 294 and the enrobed core 10 are moved a predetermined distance by the second conveyor system 298 to the seventh station 390 of the vacuum forming apparatus 292 and temporarily halted there such that the enrobed core 10 is aligned with the recess 372 and the cutting edge 376 of the second film cutter 360. As shown in FIG. 43, the second film cutter 360 is moved in the direction of the arrow UU until the enrobed core 10 is received snugly within the recess 372 and the cutting edge 376 contacts and cuts through the second film 248 closely around the perimeter of the enrobed core 10. The second film cutter 360 is then moved away from the platen 294 in a direction opposite the direction indicated by the arrow UU in FIG. 43.

Figure 44:
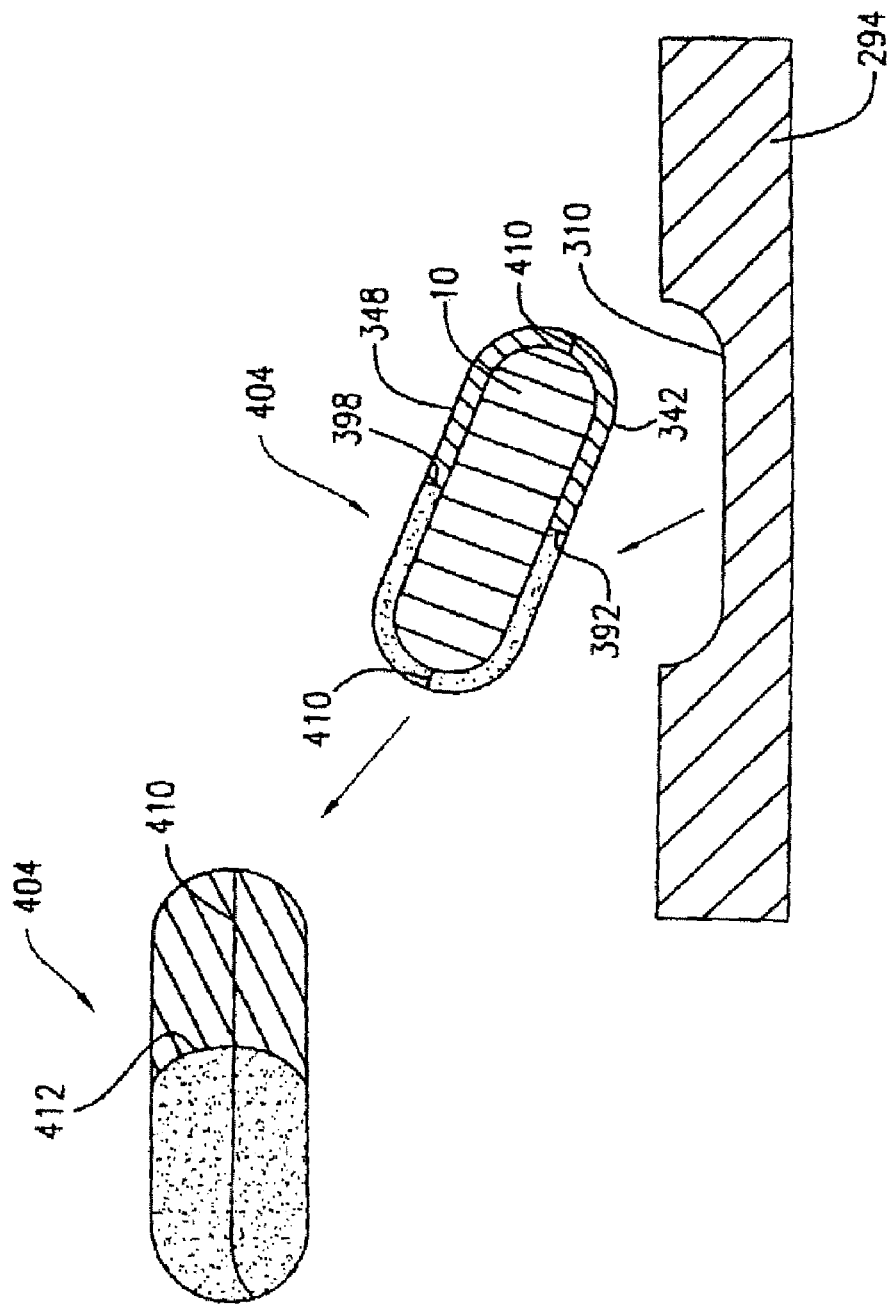
FIG. 44 is a side view of gelcaps that have film coatings that conform tightly and snugly to the cores.

As shown in FIG. 44, scrap portions 400, 402 of the second film 344 are removed from the platen 294. The platen 294 and fully enrobed core 10 are moved by the second conveyer system 298 away from the seventh station 390. After the platen 294 and enrobed core 10 are past the seventh station 390, the vacuum being applied to the platen 294 is ceased, thereby releasing the enrobed caplet product, or gelcap 404 from the recess 310.

As shown in FIG. 44, the resulting gelcaps 404 have film coatings that conform tightly and snugly to the cores 10. It is noted that, in order to form a tamper-proof seal between the first and second films 342, 348 and the core 10, an adhesive, such as a liquid form of the stock material, can be applied to the surfaces 406, 408 (see, e.g., FIGS. 36 and 41) of each of the first and second films 342, 348 that will contact the caplet 10. In addition, like the gelcaps 122, 214, 286 produced by the first, second and third embodiments of the present invention, the gelcaps 404 produced by the vacuum forming apparatus 292 and method of the fourth embodiment are bi-colored, or have at least two visually distinct regions, having a film seam 410 between the film coatings that lies substantially in the transverse plane of symmetry 16 of the core 10, and a color transition 412 between the colors, or other visually distinct regions, that lies substantially in the conjugate plane of symmetry 18 of the core 10. In addition, the color transition 412 of the gelcap 404 may be flush and seamless, i.e., without any raised portion which generally characterizes the film seam 410. In addition, the foregoing process results in gelcap products 404 having a film coating of uniform color quality and thickness over their entire surface. If aesthetically desired, the first and second films 342, 348 may be applied to the core 10 such that the resulting gelcaps 404 have a film seam 410 wherein a stripe of one color or visual distinction (for example, a red stripe) of one film 342 abuts or overlaps a stripe of another color or visual distinction (for example, a yellow stripe) of the other film 348 to form a gelcap 404 having a "checkerboard pattern" (not shown), i.e., having four quadrants of alternating red and yellow colors or other visual distinctions.

Although not shown in figures, an alternative to the apparatus and method of the fourth embodiment will now be described. The alternative apparatus would include platens having recesses that are each be circumscribed by a raised cutting ridge capable of cleanly cutting the first and second films 342, 348. In a further alternative method that may be practiced with the aforesaid apparatus, instead of first placing the caplet 10 into the recess 310 of the first platen 294, the first film 342 would be laid across a first platen and then warm air would be blown onto the first film 342 to soften it to a formable state. Then, a vacuum would be applied through the platen to pull the first film 342 into the recess and conform it thereto. Thereafter, the core 10 would be placed into the recess 310 and cool air blown onto the platen 294, first film 342 and core, to mold the first film 342 into conformity with the core 10. The second film 348 would then be placed onto the platen, on top of the core 10, and warm air blown onto the second film 348 to soften it to a formable state. Another platen (not shown) would then be moved into contact with the second film 348, pressing the second film 348 against the core 10 and the first platen 294, thereby, conforming the second film 348 to the contour of the caplet 10. Cool air is then blown onto the second film 348, thereby molding the second film 348 onto the caplet 10. It is noted that the hot and cold air temperature ranges, as well as the vacuum pressure range, are the same as previously stated hereinabove in connection with the description of the fourth embodiment of the present invention. Lastly, the raised cutting edges of the recesses cut through both of the first and second films 342, 348, thereby releasing enrobed gelcap products each of which have a film seam that is transverse to the color transition (or visual distinction transition) of the gelcaps.

The cores 10 that are suitable for use with the apparatus and methods of the present invention are mass produced and well-known by those having ordinary skill in the art. The cores enrobed with the film of the present invention may contain one or more active agents. The term "active agent" is used herein in a broad sense and may encompass any material that can be carried by or entrained in the system. For example, the active agent can be a pharmaceutical, nutraceutical, vitamin, dietary supplement, nutrient, oral care agent, herb, foodstuff, dyestuff, nutritional, mineral, supplement, or favoring agent or the like and combinations thereof.

Suitable pharmaceuticals include analgesics, anti-inflammatory agents, antiarthritics, anesthetics, antihistamines, antitussives, antibiotics, anti-infective agents, antivirals, anticoagulants, antidepressants, antidiabetic agents, antiemetics, antiflatulents, antifungals, antispasmodics, appetite suppressants, bronchodilators, cardiovascular agents, central nervous system agents, central nervous system stimulants, decongestants, diuretics, expectorants, gastrointestinal agents, migraine preparations, motion sickness products, mucolytics, muscle relaxants, osteoporosis preparations, polydimethylsiloxanes, respiratory agents, sleep-aids, urinary tract agents and mixtures thereof.

Suitable oral care agents include breath fresheners, tooth whiteners, antimicrobial agents, tooth mineralizers, tooth decay inhibitors, topical anesthetics, mucoprotectants, and the like.

Suitable flavorants include menthol, peppermint, mint flavors, fruit flavors, chocolate, vanilla, bubblegum flavors, coffee flavors, liqueur flavors and combinations and the like.

Examples of suitable gastrointestinal agents include antacids such as calcium carbonate, magnesium hydroxide, magnesium oxide, magnesium carbonate, aluminum hydroxide, sodium bicarbonate, dihydroxyaluminum sodium carbonate; stimulant laxatives, such as bisacodyl, cascara sagrada, danthron, senna, phenolphthalein, aloe, castor oil, ricinoleic acid, and dehydrocholic acid, and mixtures thereof; H2 receptor antagonists, such as famotadine, ranitidine, cimetadine, nizatidine; proton pump inhibitors such as omeprazole or lansoprazole; gastrointestinal cytoprotectives, such as sucraflate and misoprostol; gastrointestinal prokinetics, such as prucalopride, antibiotics for *H. pylori*, such as clarithromycin, amoxicillin, tetracycline, and metronidazole; antidiarrheals, such as diphenoxylate and loperamide; glycopyrrolate; antiemetics, such as ondansetron, analgesics, such as mesalamine.

In one embodiment, the active agent may be selected from bisacodyl, famotadine, ranitidine, cimetidine, prucalopride, diphenoxylate, loperamide, lactase, mesalamine, bismuth, antacids, and pharmaceutically acceptable salts, esters, isomers, and mixtures thereof.

In another embodiment, the active agent may be selected from acetaminophen, acetyl salicylic acid, ibuprofen, naproxen, ketoprofen, flurbiprofen, diclofenac, cyclobenzaprine, meloxicam, rofecoxib, celecoxib, and pharmaceutically acceptable salts, esters, isomers, and mixtures thereof.

In another embodiment, the active agent may be selected from pseudoephedrine, phenylpropanolamine, chlorpheniramine, dextromethorphan, diphenhydramine, astemizole, terfenadine, fexofenadine, loratadine, cetirizine, mixtures thereof and pharmaceutically acceptable salts, esters, isomers, and mixtures thereof.

Examples of suitable polydimethylsiloxanes, which include, but are not limited to dimethicone and simethicone, are those disclosed in U.S. Pat. Nos. 4,906,478, 5,275,822, and 6,103,260, the contents of each is expressly incorporated herein by reference. As used herein, the term "simethicone" refers to the broader class of polydimethylsiloxanes, including but not limited to simethicone and dimethicone.

The active ingredient(s) is present in the dosage form in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dose regime, the age and weight of the patient, and other factors must be considered, as known in the art. Preferably, the dosage form comprises at least about 85 weight percent of the active ingredient. In one preferred embodiment, the core comprises at least about 85 weight percent of the active ingredient.

If the active ingredient has an objectionable taste, and the dosage form is intended to be chewed or disintegrated in the mouth prior to swallowing, the active ingredient may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked active ingredients may also be employed. For example, acetaminophen particles which are encapsulated with ethylcellulose or other polymers by a coaccervation process may be used in the present invention. Coaccervation-encapsulated acetaminophen may be purchased commercially from Eurand America, Inc. Vandalia, Ohio, or from Circa Inc., Dayton, Ohio.

Suitable excipients include fillers, binders, disintegrants, lubricants, glidants, and the like.

Suitable fillers include water-soluble compressible carbohydrates such as sugars, which include dextrose, sucrose, maltose, and lactose, sugar-alcohols, which include mannitol, sorbitol, maltitol, xylitol, starch hydrolysates, which include dextrins, and maltodextrins, and the like, water insoluble plasticly deforming materials such as microcrystalline cellulose or other cellulosic derivatives, water-insoluble brittle fracture materials such as dicalcium phosphate, tricalcium phosphate and the like and mixtures thereof.

Suitable binders include dry binders such as polyvinyl pyrrolidone, hydroxypropylmethylcellulose, and the like; wet binders such as water-soluble polymers, including hydrocolloids such as alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan, polyvinyl pyrrolidone, cellulosics, starches, and the like; and derivatives and mixtures thereof.

Suitable disintegrants include sodium starch glycolate, cross-linked polyvinylpyrrolidone, cross-linked carboxymethylcellulose, starches, microcrystalline cellulose, and the like.

Suitable lubricants include long chain fatty acids and their salts, such as magnesium stearate and stearic acid, talc, and waxes. Suitable glidants include colloidal silicon dioxide, and the like.

The dosage form of this invention may also incorporate pharmaceutically acceptable adjuvants, including, for example, preservatives, sweeteners such as aspartame, acesulfame potassium, sucralose, and saccharin; flavors, antioxidants, surfactants, and coloring agents.

In one embodiment, the dosage forms comprising cores enrobed with the films of the present invention provided for immediate release of the active ingredient, i.e. the dissolution of the dosage form conformed to USP specifications for immediate release tablets containing the particular active ingredient employed. For example, for acetaminophen tablets, USP 24 specifies that in pH 5.8 phosphate buffer, using USP apparatus 2 (paddles) at 50 rpm, at least 80% of the acetaminophen contained in the dosage form is released therefrom within 30 minutes after dosing, and for ibuprofen tablets, USP 24 specifies that in pH 7.2 phosphate buffer, using USP apparatus 2 (paddles) at 50 rpm, at least 80% of the ibuprofen contained in the dosage form is released therefrom within 60 minutes after dosing. See USP 24, 2000 Version, 19-20 and 856 (1999).

It will be understood that the embodiments described hereinabove are merely exemplary and that a person skilled in the art may make many variations and modifications without departing from the spirit and scope of the present invention. All such variations and modifications are intended to be included within the scope of the invention.

I claim:

1. A process for enrobing a core comprising:
   providing a coating formed from at least one film having a thickness and a transition line segment between visually distinct portions thereof that lie on opposite sides of the transition line, wherein each of said portions has a visual distinction that substantially traverses the film thickness; and
   covering at least a portion of an outer surface of the core with at least one subcoating to form a subcoated surface;
   covering at least a portion of the subcoated surface with said at least one film such that a film seam is formed which lies substantially in a first reference plane, which passes through the core, and such that said transition line segment lies substantially in a second reference plane, which passes through the core and intersects said first reference plane, wherein said first reference plane is not congruent with said second reference plane.

2. The process according to claim 1, wherein said at least one film includes a first film having a first transition line segment between visually distinct portions thereof and a second film having a second transition line segment between visually distinct portions thereof.

3. The process according to claim 2, further comprising:
   covering a first portion of said subcoated surface with said first film such that said first transition line segment lies substantially in said second reference plane; and
   covering a second portion of said subcoated surface with said second film such that said second transition line segment lies substantially in said second reference plane.

4. The process according to claim 3, wherein said first and second transition line segments cooperate to form a transition line on said coating.

5. The process according to claim 4, wherein said first film has a first portion lying on one side of said first transition line segment and a second portion lying on an opposite side of said first transition line segment, said first and second portions of said first film being visually distinct from each other, and said second film has a first portion lying on one side of said second transition line segment and a second portion lying on an opposite side of said second transition line segment, said first and second portions of said second film being visually distinct from each other.

6. The process according to claim 5, wherein said first portion of said first film has a first visual appearance, said second portion of said first film has a second visual appearance, said first portion of said second film has a third visual appearance and said second portion of said second film has a fourth visual appearance.

7. The process according to claim 6, wherein said first visual appearance of said first portion of said first film is substantially the same as said third visual appearance of said first portion of said second film, and second visual appearance of said second portion of said first film is substantially the same as said fourth visual appearance of said second portion of said second film, said first and third visual appearances being different from said second and fourth visual appearances.

8. The process according to claim 7, further comprising:
   orienting said first and second films, prior to covering the subcoated surface, such that said first portions of said first and second films lie on one side of said transition line of said coating, whereby said first portions are adjacent to one another and positioned on opposite sides of said film seam, and said second portions of said first and second films lie on an opposite side of said transition line of said coating, whereby said second portions are adjacent to one another and positioned on opposite sides of said film seam.

9. The process according to claim 8, wherein said first and third visual appearances are characterized by a first color and said second and fourth visual appearances are characterized by a second color that is different from said first color, whereby said coating of the enrobed core includes at least two differently colored portions.

10. The process according to claim 7, further comprising:
    orienting said first and second films, prior to covering the subcoated surface, such that said first portion of said first film and said second portion of said second film lie on one side of said transition line, whereby said first portion of said first film and said second portion of said second film are adjacent to one another and positioned on opposite sides of said film seam, and said second portion of said first film and said first portion of said second film lie on an opposite side of said transition line, whereby said second portion of said first film and said first portion of said second film are adjacent to one another and positioned on opposite sides of said film seam.

11. The process according to claim 10, wherein said first and third visual appearances are characterized by a first color and said second and fourth visual appearances are characterized by a second color that is different from said first color, whereby said coating of the enrobed core includes at least four colored portions that are alternately arranged on said coating.

12. The process according to claim 3, wherein each of said first and second films includes free edges.

13. The process according to claim 12, wherein said free edges are slightly spaced apart from one another, thereby forming said film seam of said coating.

14. The process according to claim 12, further comprising:
sealing said free edges of said first and second films together, thereby forming said film seam of said coating.

15. The process according to claim 14, wherein said free edges of said first and second films abut one another to form said film seam of said coating.

16. The process according to claim 14, wherein said free edges of said first and second films overlap with one another to form said film seam of said coating.

17. The process according to claim 3, wherein said transition line of said coating is curvilinear.

18. The process according to claim 1, wherein said transition line segment is curvilinear.

19. The process according to claim 1, wherein the core is a tablet.

* * * * *